United States Patent [19]

Baggiolini, deceased et al.

[11] Patent Number: 5,087,619

[45] Date of Patent: Feb. 11, 1992

[54] VITAMIN $D_3$ ANALOGS

[75] Inventors: Enrico G. Baggiolini, deceased, late of North Caldwell, N.J., by Barbara Judith Baggiolini, Executrix; Barbara J. Baggiolini, North Caldwell, N.J.; Bernard M. Hennessy, Nutley, N.J.; Shian-Jan Shiuey, Nutley, N.J.; Gary A. Truitt, Bloomfield, N.J.; Milan R. Uskokovic, Upper Montclair, N.J.

[73] Assignee: Hoffman-La Roche Inc., Nutley, N.J.

[21] Appl. No.: 498,062

[22] Filed: Mar. 23, 1990

Related U.S. Application Data

[63] Continuation-in-part of Ser. No. 353,716, May 18, 1989, abandoned, which is a continuation-in-part of Ser. No. 160,798, Feb. 26, 1988, abandoned, which is a continuation-in-part of Ser. No. 145,932, Jan. 20, 1988, abandoned.

[51] Int. Cl.$^5$ .................. A01N 45/00; C07J 172/00; C07J 175/00; C07F 7/04
[52] U.S. Cl. .................. 514/167; 552/653; 556/436; 514/859; 514/863; 514/864; 514/908
[58] Field of Search .................. 514/167; 552/653; 556/436

[56] References Cited

U.S. PATENT DOCUMENTS

| | | | |
|---|---|---|---|
| 4,391,802 | 7/1983 | Suda et al. | 514/167 |
| 4,804,502 | 2/1989 | Baggiolini | 514/167 |
| 4,851,400 | 7/1989 | DeLuca | 514/167 |

FOREIGN PATENT DOCUMENTS

| | | |
|---|---|---|
| 0129003 | 12/1984 | European Pat. Off. . |
| 0215956 | 3/1986 | European Pat. Off. . |
| 0307786 | 3/1989 | European Pat. Off. . |

OTHER PUBLICATIONS

Janistyn, "Handbuch der Kosmetika and Riechstoffe".
K. Schaefer, D. Von Herrath, "Vitamin D 1980-Eine Bestandsaufnahme".
Malloy et al., pp. 475, the Journal of Investigative Dermatology, 3/89, vol. 92, No. 3.
Endocrinology 112: 200–206, 1983.
Cancer Research 43(8): 4989–4996, 1983.
J. Cell. Biol. 97(5): 347a, 1983.
Blood 62(5): 153a, 1983.
Cancer Research 43(12), 5862–5867, 1983.
Lancet, Dec. 22/29: 1335–1336, 1979.
Cancer Research 42: 1116–119, 1982.
Cancer Research 42: 856–859, 1982.
Biochem J. 200: 315–320, 1981.
Cancer Research 43: 4443, 4447, 1983.
Arch. Biochem, Biophys., 220:90–94, 1983.
Proc. Natl. Acad. Sci.: U.S.A. 78: 4990–4994, 1981.
Exp. Hematol. 11 (Suppl. 14): 200, 1983.
Proc. Natl. Acad. Sci., U.S.A. 80: 201–204, 1983.
Tohoku, J. Exp. Med., 138: 445–446, 1982.
Lancet, Jan. 14: 78–80, 1984.
Cancer Res. 47(6): 567–572, 1987.
Cancer Res. 47: 21–25, 1987.

*Primary Examiner*—Frederick E. Waddell
*Assistant Examiner*—T. J. Criares
*Attorney, Agent, or Firm*—George M. Gould; George W. Johnston; Ellen Ciambrone Coletti

[57] ABSTRACT

Compounds of the formula

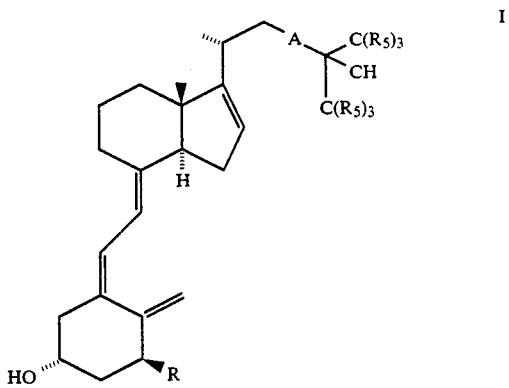

wherein R is hydrogen or hydroxy, $R_5$ is hydrogen, and A is —C≡C—,

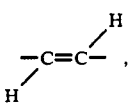

or —CH$_2$—CH$_2$—, with the proviso that when A is —C≡C—, $R_5$ may also be deuterium, are described.

The compounds of formula I are useful as agents for the treatment of hyperproliferative disorders of the skin such as psoriasis, as agents for the treatment of neoplastic diseases such as leukemia, and as agents for the treatment of sebaceous gland diseases such as acne or seborrheic dermatitis.

39 Claims, No Drawings

VITAMIN D₃ ANALOGS

CROSS-REFERENCE TO RELATED APPLICATION

This is a continuation-in-part of application Ser. No. 353,716 filed May 18, 1989, now abandoned, in turn is a continuation-in-part of application Ser. No. 160,798, filed Feb. 26, 1988, now abandoned, which in turn is a continuation-in-part of application Ser. No. 145,932 filed Jan. 20, 1988, now abandoned.

BRIEF SUMMARY OF THE INVENTION

The invention relates to compounds of the formula

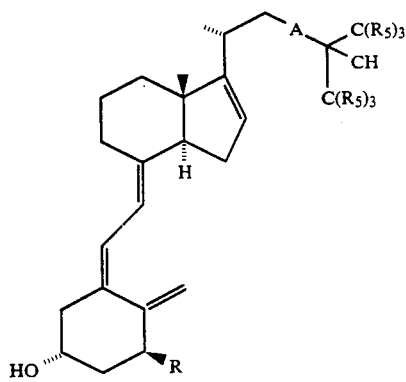

wherein R is hydrogen or hydroxy, $R_5$ is hydrogen, and A is —C≡C—,

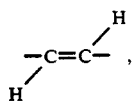

or —CH₂—CH₂—; with the proviso that when A is —C≡C—, $R_5$ may also be deuterium.

Compounds of formula I as described above are useful as agents for the treatment of hyperproliferative skin diseases such as psoriasis. Compounds of formula I as described above are also useful as agents for the treatment of neoplastic diseases such as leukemia. Compounds of formula I are also useful as agents for the treatment of sebaceous gland diseases such as acne or seborrheic dermatitis.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, t-butyl and the like. Alternatively, the number of carbon atoms in an alkyl group is designated herein as in "$C_1$-$C_3$ alkyl" which denotes a straight or branched-chain alkyl group containing 1 to 3 carbon atoms. The term "ar-lower alkyl" denotes a lower alkyl group which is substituted by an aryl group. Exemplary of "ar-lower alkyl" are p-tolyl, benzyl, phenylethyl, phenylpropyl, and the like. The term "aryl" denotes a group derived from an aromatic hydrocarbon which may be unsubstituted or substituted by one or more lower alkyl groups. Exemplary of "aryl" are phenyl and p-methyl phenyl. The term "halogen" denotes the halogens, that is, bromine, chlorine, fluorine, or iodine.

In the formulas presented herein, the various substituents are illustrated as joined to the nucleus by one of the following notations: a wedged solid line ( ) indicating a substituent which is above the plane of the molecule, (β-orientation) and a wedged dotted line ( ) indicating a substituent which is below the plane of molecule (α-orientation).

As used herein, the term "trans" denotes,

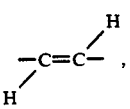

that is, a stereochemical configuration about a carbon-carbon double bond, such that the two hydrogens are attached to different carbon atoms, and are on opposite sides of the carbon-carbon double bond.

The invention relates to compounds of the formula

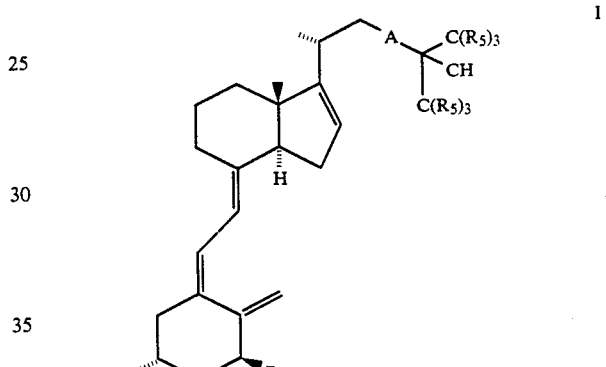

wherein R is hydrogen or hydroxy; $R_5$ is hydrogen and A is —C≡C—,

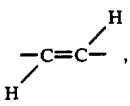

or —CH₂—CH₂—; with the proviso that when A is —C≡C—, $R_5$ may also be deuterium.

Compounds of formula I as described above stimulate differentiation and decrease proliferation of human keratinocytes. Accordingly, compounds of formula I as described above are useful as agents in the treatment 354 of hyperproliferative skin disorders such as psoriasis, basal cell carcinomas, disorders of keratinization, and keratosis. The compounds of formula I are also useful as agents in the treatment of neoplastic diseases such as leukemia. The compounds of formula I are also useful as agents for the treatment of sebaceous gland diseases such as acne or seborrheic dermatitis.

The invention also relates to a composition comprising a compound of formula I, or a mixture of two or more compounds of formula I.

The invention also relates to a method for treating the above-mentioned disease states by administration of a compound or formula I, or a mixture of two or more compounds of formula I.

The invention also relates to a process for preparing compounds of formula I as described above.

Compounds of formula I of the invention are:
1α,25-hydroxy-16-ene-cholecalciferol;
25-dihydroxy-16,23E-diene-cholecalciferol;
25-hydroxy-16,23E-diene-cholecalciferol;
25-dihydroxy-16-ene-23-yne-cholecalciferol;
1α,25-dihydroxy-16-ene-23-yne-cholecalciferol;
26,26,26,27,27,27-hexadeutero-1α,25-dihydroxy-16-ene-23-yne-cholecalciferol; and
26,26,26,27,27,27-hexadeutero-25-hydroxy-16-ene-23-yne-cholecalciferl.

The compounds of formula I wherein $R_5$ are hydrogen are prepared as hereafter described, with particular reference to the Formula Schemes below.

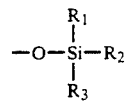

wherein $R_1$, $R_2$, and $R_3$ are as described above.

The reaction is carried out at $-60°$ C.$--90°$ C., preferably $-75°$ C., in a polar, aprotic, organic solvent, such as dry ether or more preferably dry tetrahydrofuran, in the presence of a strong base such as an alkyl lithium like butyl lithium.

Compounds of formula III are known or can be pre-

FORMULA SCHEME 1

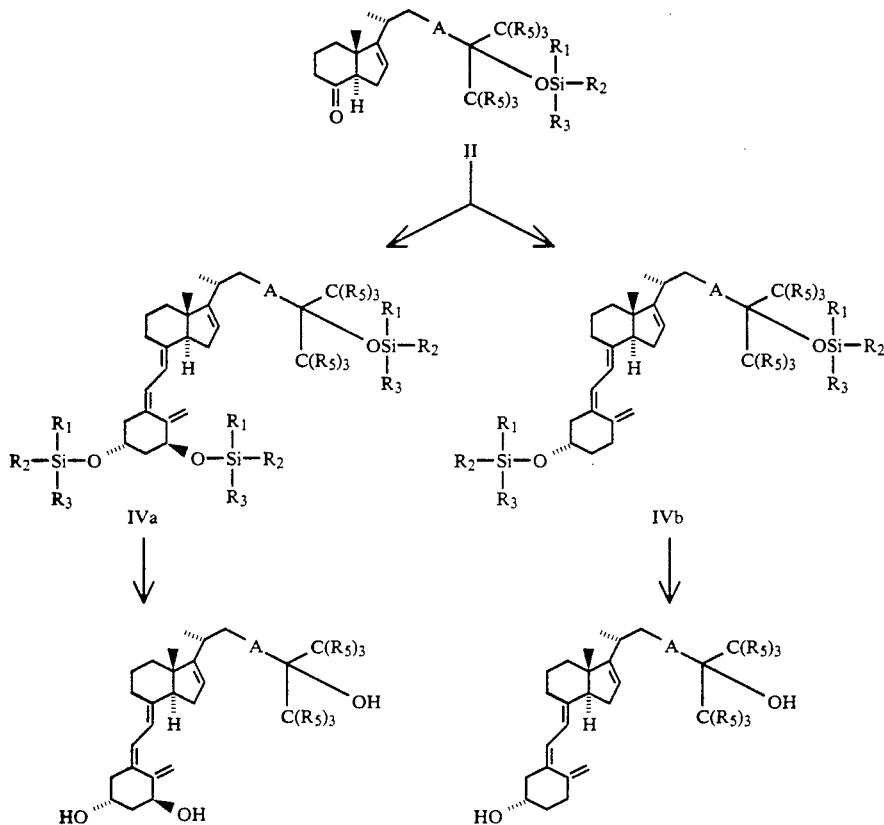

wherein A is as described above and $R_1$ and $R_3$ are independently lower alkyl and $R_2$ is independently lower alkyl, aryl, or ar-lower alkyl.

In above Formula Scheme I, the compound of Formula II is converted to a compound of formula IVa or IVb by reaction with the corresponding compound of formula

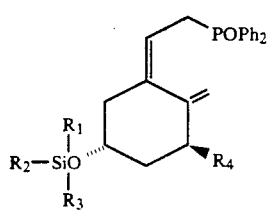

where Ph is phenyl; and $R_1$, $R_2$ and $R_3$ are as described above; $R_4$ is hydrogen or pared in accordance with known methods.

The protecting groups of a compound of formula IVa or IVb are removed by reaction with a fluorine salt, such as tetrabutyl-ammonium fluoride in a polar, organic solvent such as ether, or more preferably tetrahydrofuran, to yield a corresponding compound of formula Ia or Ib,

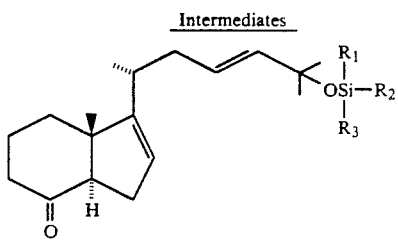

and

-continued
Intermediates

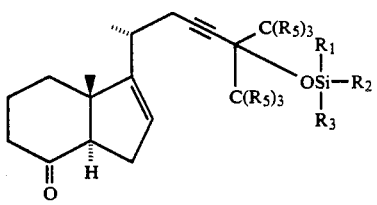
IIb wherein $R_1$, $R_2$, $R_3$ and $R_5$ are as described above are prepared as hereafter described, with particular reference to Formula Scheme II below.

FORMULA SCHEME II

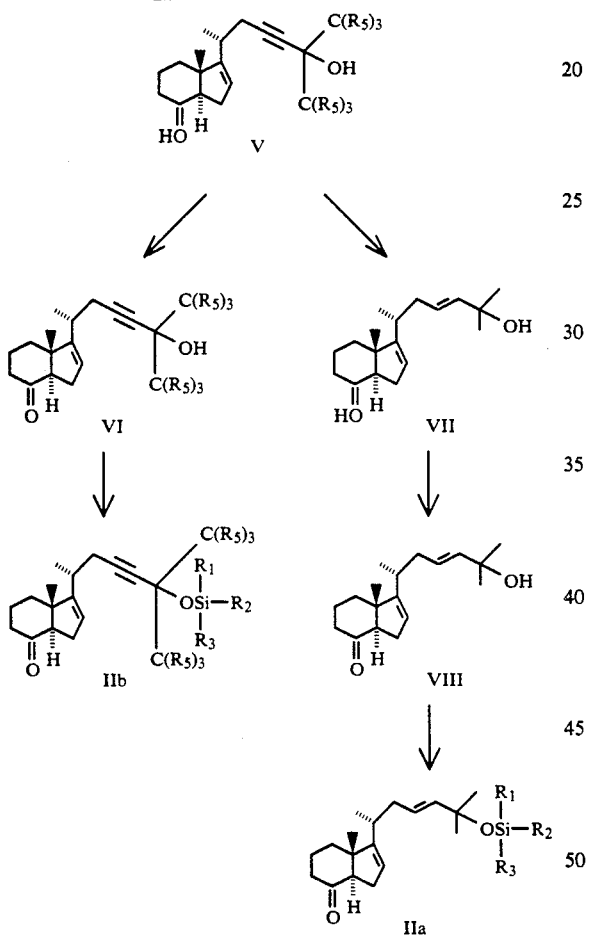

wherein $R_1$, $R_2$, $R_3$ and $R_5$ are as described above.

In above Formula Scheme II, the compound of formula V is oxidized to the compound of formula VI by treatment with an oxidizing agent such as 2,2'-bipyridinium chlorochromate, or more preferably, pyridinium chlorochromate, at room temperature, in an aprotic, organic solvent such as dry methylene chloride.

The compound of formula VI is converted to a compound of formula IIb, by reaction with, for example, a (trialkylsilyl)imidazole such as (trimethylsilyl)imidazole in an aprotic, organic solvent such as dry tetrahydrofuran, or more preferably, dry methylene chloride. The compound of formula IIb is worked up and purified by conventional means such as extraction followed by chromatography.

The compound of formula V may also be partially hydrogenated to obtain the compound of formula VII by reaction with a reducing agent such as lithium aluminum hydride, preferably in the presence of an alkali metal alkoxide, like sodium methoxide, in an aprotic organic solvent like dry ether, or more preferably dry tetrahydrofuran, at reflux temperature (about 68° C. for tetrahydrofuran) for about 10-20 hours, cooled to about 0° C., and worked up by conventional means.

The resulting compound of formula VII is oxidized to the compound of formula VIII by treatment with an oxidizing agent such as 2,2'-bipyridinium chlorochromate, or pyridinium chlorochromate, at room temperature, in an aprotic, organic solvent such as dry tetrahydrofuran, or more preferably, dry methylene chloride.

The compound of formula VIII is converted to a compound of formula IIa, by reaction with, for example, a (trialkylsilyl)imidazole such as (trimethylsilyl)imidazole in an aprotic, organic solvent such as dry tetrahydrofuran, or more preferably, dry methylene chloride. The compound of formula IIa is worked up by conventional means such as extraction followed by chromatography.

Intermediates IIc are prepared as hereafter described, with particular reference to Formula Scheme III below.

FORMULA SCHEME III

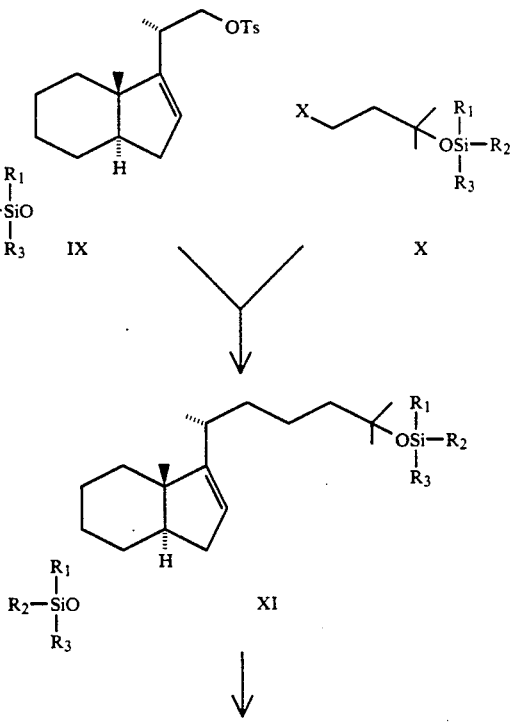

-continued
FORMULA SCHEME III

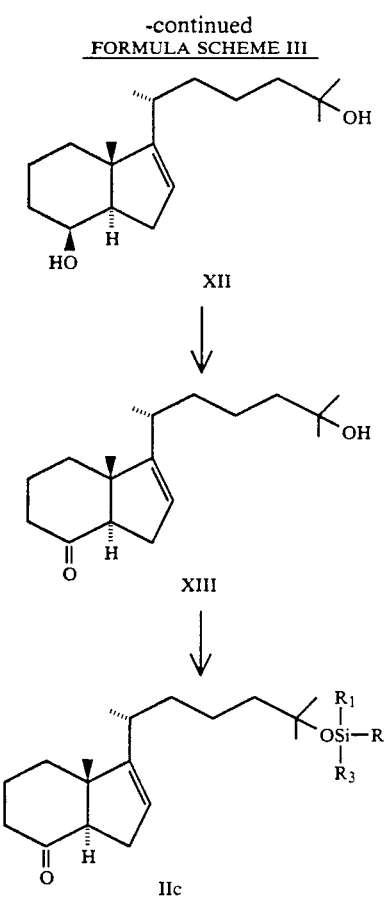

wherein $R_1$, $R_2$ and $R_3$ are as described above, X is chlorine, bromine or iodine and Ts is tosyl.

In above Formula Scheme III, the compound of formula X is reacted in dry ether, or more preferably dry tetrahydrofuran at reflux temperature with magnesium. The resulting Grignard solution is treated with cuprous iodide and then compound of formula IX is added. This reaction yields a compound of formula XI upon conventional work-up and purification such as extraction followed by chromatography.

A compound of formula XI is reacted with a fluoride salt, such as tetrabutylammonium fluoride in dry ether, or more preferably dry tetrahydrofuran to give a compound of formula XII.

A compound of formula XII may be oxidized by reaction with an oxidizing agent such as 2,2'-bipyridinium chlorochromate or pyridinium chlorochromate, at room temperature, in an aprotic, organic solvent such as dry methylene chloride. The compound of formula XIII results upon conventional work-up and chromatographic purification.

The compound of formula XIII is converted to a compound of formula IIc, by reaction with, for example, a (trialkylsilyl)imidazole such as (trimethylsilyl)imidazole in an polar, aprotic, organic solvent such as dry tetrahydrofuran, or more preferably, dry methylene chloride. A compound of formula IIc is worked-up and purified by conventional means such as extraction followed by chromatography.

A compound of formula IX, which serves as a starting material in Formula Scheme III above, can be prepared as follows from the compound of formula

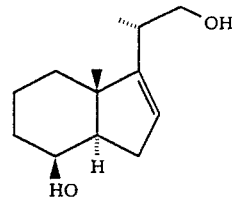

which is known [P. M. Wovkulich, F. Barcelos, A. D. Batcho, J. F. Sereno, E. G. Baggiolini, B. M. Hennessy and M. R. Usuokovic', Tetrahedron 40, 2283 (1984)] by reaction with a tosylating agent such as a p-toluenesulfonyl halide like p-toluenesulfonyl chloride in an organic base like dry collidine, or more preferably, dry pyridine to give the compound of formula

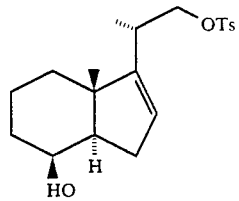

The compound of formula XV is then converted to a compound of formula IX by reaction of a trialkylsilyl chloride such as trimethylsilyl chloride in the presence of imidazole and in an aprotic organic solvent like tetrahydrofuran or methylene chloride.

A compound of formula X in Formula Scheme III above is prepared as follows. A compound of formula

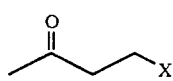

wherein X is as described above, which is known or can be prepared in accordance with known methods is converted to a compound of formula

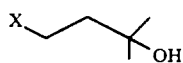

wherein X is as described above, by reaction with a methyl Grignard reagent such as methylmagnesium bromide in ether.

The compound of formula XVII is then converted to a compound of formula X, by reaction with a trialkylsilyl chloride such as trimethylsilyl chloride in the presence of imidazole and in an aprotic organic solvent like tetrahydrofuran or methylene chloride.

The compound of formula V as set forth in Formula Scheme II above is prepared as follows.

The compound of formula

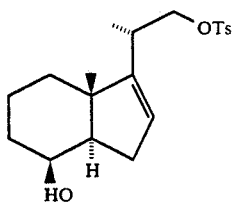
XV which is prepared as described above, is reacted with a cyanide forming agent such as sodium cyanide in an aprotic, organic solvent such as dimethyl sulfoxide at a temperature between 80°-100° C. for 1 to 5 hours to give, after conventional work-up and purification, a compound of formula

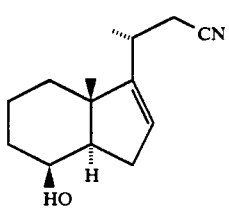
XVIII

The compound of formula XVIII is converted to the compound of formula

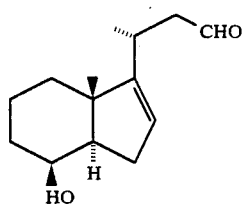
XIX by reaction with a reducing agent, such as diisobutylaluminum hydride, followed by hydrolysis with, for example, a mineral acid such as hydrochloric acid. The reaction with reducing agent is conducted in an aprotic, organic solvent such as dry methylene chloride at about −10° to about 10° C. for about 30 minutes to 1 ½ hours.

The compound of formula XIX is converted to the compound of formula

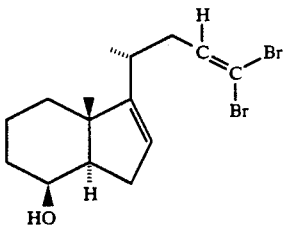
XX by reaction with a mixture of triphenylphosphine, carbon tetrabromide and zinc dust, in an aprotic organic solvent such as dry methylene chloride, for about 1 to about 30 hours, at about room temperature, followed by a conventional work-up and purification. The mixture of triphenylphosphine, carbon tetrabromide and zinc dust, is stirred in methylene chloride for 20 to 40 hours just prior to the above-described reaction with the compound of formula XIX.

The compound of formula XX is converted to the compound of formula

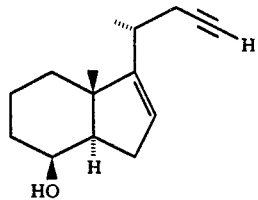
XXI by reaction with a strong base such as butyllithium, in a polar, aprotic solvent such as dry tetrahydrofuran, at about −80° to about −70° C., for about 1 to about 3 hours. The resulting compound of formula XXI is worked up by conventional means and purified by conventional means such as chromatography.

The compound of formula XXI is converted to the compound of formula

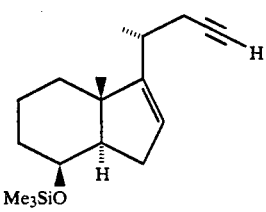
XXII by reaction with (trimethylsilyl)imidazole in an aprotic, organic solvent such as dry tetrahydrofuran, or more preferably, dry methylene chloride. The compound of formula XXII is worked up and purified by conventional means such as extraction followed by chromatography.

The compound of formula XXII is converted to the compound of formula

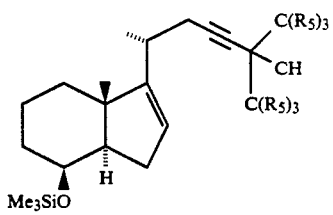
XXIII where $R_5$ is hydrogen or deuterium, by reaction with a strong base such as butyllithium and then acetone or hexadeutersacetone. The reaction is conducted in an aprotic, organic solvent such as dry tetrahydrofuran at about −80° to about −60° C. The compound of formula XXIII is recovered by quenching the reaction, followed by a conventional work-up and a purification as by chromatography.

The compound of formula XXIII is deprotected to give the compound of formula

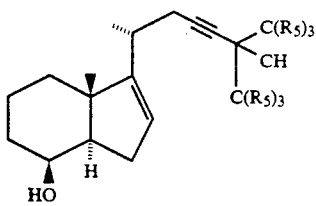

where $R_5$ is hydrogen or deuterium, by reaction with a fluorine salt such as tetrabutyl-ammonium fluoride in an organic solvent such as ether, or more preferably tetrahydrofuran.

The compounds of formula I as described above can be administered orally, for the treatment of neoplastic diseases such as leukemia, to warmblooded animals which need such treatment. More specifically, the compounds of formula I as described above can be administered orally to an adult human in dosages that are in the range of about 0.1 to 10 μg per day for the treatment of neoplastic diseases such as leukemia.

The compounds of formula I as described above can be administered orally, for the treatment of hyperproliferative skin diseases such as psoriasis, basal cell carcinomas, disorders of keratinization, and keratosis, to warmblooded animals which need such treatment. More specifically, the compounds of formula I as described above can be administered orally to an adult human in dosages that are in the range of about 0.1 to 1000 μg per day for the treatment of hyperproliferative skin diseases such as psoriasis, basal cell carcinomas, disorders or keratinization, and keratosis. These compounds can be administered orally for the treatment of acne in humans at a dosage of about 0.7 to 700 μg per day; preferably 7.0 to 70 μg per day.

The compounds of formula I as described above can be administered topically, for the treatment of hyperproliferative skin diseases such as psoriasis, basal cell carcinomas, disorders of keratinization, and keratosis, to warmblooded animals which need such treatment. More specifically, the compounds of formula I as described above can be administered topically in dosages that are in the range of about 1 to about 1000 μg per gram of topical formulation per day, for the treatment of hyperproliferative skin diseases such as psoriasis, basal cell carcinomas, disorders of keratinization, and keratosis.

The compounds of formula I as described above can also be administered topically for the treatment of sebaceous gland diseases such as acne or seborrheic dermatitis.

The compounds of formula I as described above can also be administered orally for the treatment of sebaceous gland diseases such as acne or seborrheic dermatitis.

The useful activity of compounds of formula I as agents for the treatment of hyperproliferative skin diseases can be demonstrated by the following test procedures which are known in the art, and which are also set forth in The Society for Investigative Dermatology (1986) p. 709–714 Holick et al.

Effect of Compounds of Formula I on the Morphologic Differentiation of Cultured Human Keratinocytes Keratinocyte Culture—Keratinocytes were grown in culture using a modification of the method of Rheinwald and Green. 3T3 cells were plated at $0.5 \times 10^5$ cells/35 mm tissue culture dish and 2 days later were lethally irradiated with a cobalt 60 source (5000 rads). Keratinocytes were obtained from human neonatal foreskin after overnight trypsinization at 4° C. and treatment with 0.02% EDTA. Keratinocytes were plated in 2 ml of serum-free medium per dish on the lethally irradiated 3T3 cells. Each experiment was performed on primary or secondary keratinocyte cultures obtained from different skin samples. The serum-free medium consisted of Dulbecco's modified Eagle's medium (DMEM) with high (1.8 mm) concentration of calcium (M. A. Bioproducts, Walkersville, Md.) containing 7 growth factors; epidermal growth factor (25 ng/ml); hydrocortisone (203 ng/ml); insulin (5 μg/ml); transferring (5 μg/ml); prostaglandin $E_1$ (50 mg/ml); cholera toxin (0.1 μg/ml; Sigma Chemical Co., St. Louis, Mo.); and selenous acid (2 ng/ml; Collaborative Research, Lexington, Mass.). At 1 week in culture, hydrocortisone and cholera toxin were removed from the medium, and the dishes were washed with 0.02% EDTA to remove any remaining 3T3 cells. For the various assays, fresh medium containing vehicle (that is →0.1% absolute ethanol) and the compound to be tested at the concentrations given in table I below was added to each dish with each feeding. Feedings were done three times a week. For the control, fresh medium containing vehicle alone, that is, →0.1% absolute ethanol was used.

Quantitation of Morphologic Changes During Keratinocyte Differentiation.

Beginning at 1 week in culture, groups of triplicate plates of keratinocytes were incubated with compounds A or B at the concentrations given in Table I below. After 1 or 2 weeks of dosing, the medium was removed from each culture, centrifuged, and resuspended for the counting of the desquamated floater cells. A hemacytometer was used to count the different cell types under a phase-contrast microscope. The attached cells were then trypsinized for 30-40 minutes with 0.1% EDTA and 0.1% trypsin and then neutralized with medium. The keratinocytes were centrifuged and resuspended in a known volume of medium. Duplicate aliquots were taken for counting the basal (small, rounded) and squamous (larger, irregular-shaped, flattened) cells. The remaining cells were centrifuged and treated with 10 mM Tris-HCl (pH 7.4) with 1% β-mercaptoethanol and 1% sodium dodecyl sulfate (SDS) at room temperature for 10 minutes. Only cells with cornified envelopes were present after this treatment. These were counted by hemacytometer.

A compound which induces the differentiation of basal cells to squamous and envelope cells is useful as an agent in the treatment of skin diseases characterized by disorders of keratinization such as psoriasis.

The results of the above tests are shown in TABLE I just below.

TABLE I

| | Conc. Metabolite | Total | Basal | Squamous | Envelopes |
|---|---|---|---|---|---|
| Control | | 133 ± 5 | 118 ± 4 | 15 ± 1 | 18 ± 2 |
| 1α,25-Dihydroxy | $10^{-10}$M | 122 ± 4 | 103 ± 2 | 19 ± 2 | 23 ± 1 |
| cholecalciferol | $10^{-8}$M | 112 ± 6 | 89 ± 2 | 23 ± 4 | 30 ± 3 |
| | $10^{-6}$M | 95 ± 7 | 64 ± 6 | 31 ± 1 | 34 ± 2 |
| 1α,25-Dihydroxy- | $10^{-10}$M | 132 ± 8 | 115 ± 7 | 17 ± 1 | 27 ± 2 |
| $\Delta^{16}$-chole- | $10^{-8}$M | 128 ± 10 | 106 ± 8 | 22 ± 2 | 33 ± 2 |
| calciferol | $10^{-6}$M | 101 ± 7 | 71 ± 5 | 30 ± 2 | 39 ± 2 |
| 25-Hydroxy-$\Delta^{16}$- | $10^{-10}$M | 133 ± 6 | 115 ± 5 | 18 ± 1 | 25 ± 1 |
| cholecalciferol | $10^{-8}$M | 131 ± 4 | 109 ± 2 | 22 ± 2 | 29 ± 2 |
| | $10^{-6}$M | 104 ± 4 | 74 ± 3 | 30 ± 1 | 33 ± 1 |
| Control | | 123 ± 7 | 105 ± 6 | 18 ± 1 | 74 ± 7 |
| 1α,25-Dihydroxy | $10^{-10}$M | 116 ± 9 | 95 ± 8 | 21 ± 1 | 91 ± 4 |
| cholecalciferol | $10^{-8}$M | 101 ± 10 | 75 ± 8 | 26 ± 2 | 122 ± 11 |
| | $10^{-6}$M | 83 ± 5 | 57 ± 4 | 26 ± 1 | 146 ± 16 |
| 1α,25-Dihydroxy- | $10^{-10}$M | 117 ± 4 | 92 ± 2 | 25 ± 2 | 103 ± 6 |
| $\Delta^{16}$, $\Delta^{23}$- | $10^{-8}$M | 108 ± 3 | 80 ± 2 | 28 ± 1 | 128 ± 3 |
| cholecalciferol | $10^{-6}$M | 80 ± 7 | 54 ± 6 | 26 ± 1 | 153 ± 1 |
| 25-Hydroxy-$\Delta^{16}$, | $10^{-10}$M | 113 ± 7 | 93 ± 6 | 20 ± 1 | 104 ± 10 |
| $\Delta^{23}$-cholecal- | $10^{-8}$M | 111 ± 7 | 86 ± 3 | 25 ± 2 | 128 ± 5 |
| ciferol | $10^{-6}$M | 94 ± 3 | 68 ± 1 | 26 ± 2 | 144 ± 7 |
| Control | | 108 ± 10 | 93 ± 8 | 15 ± 2 | 88 ± 8 |
| 1α,25-Dihydroxy- | $10^{-10}$M | 106 ± 7 | 86 ± 6 | 18 ± 1 | 100 ± 9 |
| cholecalciferol | $10^{-8}$M | 84 ± 8 | 61 ± 5 | 23 ± 3 | 122 ± 8 |
| | $10^{-6}$M | 73 ± 7 | 51 ± 5 | 22 ± 2 | 142 ± 11 |
| 1α,25-Dihydroxy- | $10^{-10}$M | 86 ± 4 | 63 ± 2 | 23 ± 2 | 114 ± 5 |
| $\Delta^{16}$-23-yne- | $10^{-8}$M | 82 ± 3 | 53 ± 2 | 29 ± 1 | 141 ± 5 |
| cholecalciferol | $10^{-6}$M | 78 ± 3 | 41 ± 1 | 27 ± 2 | 147 ± 4 |
| 25-hydroxy-$\Delta^{16}$- | $10^{-10}$M | 103 ± 5 | 81 ± 3 | 22 ± 2 | 103 ± 4 |
| 23-yne-chole- | $10^{-8}$M | 97 ± 3 | 67 ± 2 | 29 ± 1 | 121 ± 6 |
| calciferol | $10^{-6}$M | 84 ± 4 | 55 ± 2 | 29 ± 1 | 137 ± 7 |

Human Keratinocytes in Culture, Number of Cells × $10^4$

The useful activity of compounds of formula I as agents for the treatment of hyperproliferative skin diseases can also be demonstrated by the following test procedures.

Materials and Methods

1. Culture Conditions

Human neonatal foreskins were collected by circumcision and placed into tubes containing DMEM media with 10% serum. On arrival at the laboratory they were mechanically trimmed of excess dermis, treated with a solution of trypsin/EDTA (0.05%/0.02%) at 4° C. overnight. The epidermis was stripped from the dermis, agitated in buffered saline to remove basal keratinocytes and the stratum corneum layer removed. The separated cells were centrifuged, resuspended in media, counted and cells plated onto either plain plastic or onto Mitomycin C treated 3T3 cells as appropriate (Rheinwald and Green, H. Cell 6:331-334, 1975). The keratinocytes were plated at a density of approximately 20,000 cells/cm² in dishes or wells of assorted size depending on the experiments. Cells were grown in keratinocyte growth media (KGM-modified MCDB 153; Clonetics) according to protocols developed by Boyce and Ham (In Vitro Models for Cancer Research III. 246-274, 1986) for MCDB 153 media. After cells reached confluency they were then cultured in Dulbecco's modified Eagle's medium (DMEM) without serum, supplemented with the following growth factors: epidermal growth factor (EGF), hydrocortisone, insulin, transferring, prostaglandin El, cholera toxin, and selenous acid (Smith et al. J. Invest. Dermat. 86:709-714 1986). This media will subsequently be referred to as DMEM/H. All cultures are incubated in humidified atmosphere of 5% $CO_2$ at 37° C. with media changed three times per week.

A squamous carcinoma cell line (SCC-15) was obtained from ATCC. The cells are grown in DMEM:-Ham's F10 media plus 10% FCS (fetal calf serum) and antibiotics (gentimycin, penicillin and streptomycin). Subsequent culture conditions and experiments with this cell line are similar to that of the human keratinocytes.

Solutions of the test compounds were prepared as follows: 1 milligram quantities were received in amber glass vials, and stored at −20° C. Sufficient 100% ethanol was added directly to vials to obtain a millimolar solution that was subsequently aliquoted into small amber vials, overlayed with argon gas and stored at 20° C. Each stock solution was thawed once, used and discarded. Aliquots from the stock solutions were diluted directly into medium and then serially diluted from micromolar to $10^{-12}$M concentrations. Dilutions from $10^{-8}$M to $10^{-12}$M had ethanol added for a final concentration of 0.1%. Stock solutions were used within one month. Control cultures were treated with 0.1% ethanol.

3. Cell Proliferation

For each experiment every culture dish or well received the same number of cells from the same culture source. At the termination of the experiment the number of cells per dish/well was determined by the following procedure. Dishes were washed with PBS, incubated for approximately 30 minutes with a trypsin/EDTA solution. Cells were suspended, an aliquot placed into isotonic buffered saline (S/P) and counted on an electronic particle counter (Coulter Counter). The counter was periodically calibrated to correspond to hemacytometer counts of keratinocytes. Each dish was counted at least three times and all treatments including controls were done in at least triplicate. The number of cells per dish was calculated according to the dilution factors used.

Envelopes

After removing an aliquot of cells for counting a solution of SDS/DTT was added to the cells for a final concentration of 1% SDS/5mM DTT. The cells were solubilized for one hour at 37° C. and an aliquot removed for enumeration. Aliquots were counted either with a hemacytometer or placed into isotonic buffered saline and counted with a Coulter Counter.

TABLE II

Human Keratinocytes in Culture

| Treatment | Dose (M) | Cell No. ($\times 10^4$) ± Std. Dev. | Envel. No. ($\times 10^2$) ± Std. Dev. |
| --- | --- | --- | --- |
| Controls (0.1% ETOH) | | 189.49 ± 22.3 | 858.28 ± 185.70 |
| 1α,25-Dihydroxy- $\Delta^{16}$-23-yne-cholecalciferol | $10^{-12}$ | 187.36 ± 15.33 | 1136.63 ± 383.66 |
| | $10^{-10}$ | 175.34 ± 10.19 | 1444.87 ± 312.47 |
| | $10^{-8}$ | 145.79 ± 15.66 | 2113.62 ± 1049.33 |
| | $10^{-6}$ | 41.95 ± 7.53 | 1916.83 ± 887.66 |
| Controls (0.1% ETOH) | | 148.73 ± 16.23 | 2193.7 ± 921.9 |
| 1α,25-Dihydroxy- $\Delta^{16}$-cholecalciferol | $10^{-12}$ | 114.91 ± 10.95 | 1662.2 ± 420.1 |
| | $10^{-10}$ | 130.37 ± 24.32 | 3973.8 ± 126.99 |
| | $10^{-8}$ | 120.67 ± 16.87 | 7235.2 ± 55.5 |
| | $10^{-8}$ | 109.22 ± 15.87 | 8323.5 ± 157.6 |

Human keratinocytes grown in DMEM/H in the presence of test compound for two weeks. Average number of cells per well and average number of envelopes formed per well were determined for each separate experiment.

TABLE III

HUMAN SQUAMOUS CARCINOMA CELL LINE (SCC-15)

| Treatment | Dose (M) | Cell Number ($\times 10^{-5}$) ± Std. Error |
| --- | --- | --- |
| Control | | 7.35 ± 1.75 |
| 1α,25-Dihydroxy-$\Delta^{16}$-23-yne-cholecalciferol | $10^{-12}$ | 6.98 ± 1.68 |
| | $10^{-10}$ | 5.89 ± 1.58 |
| | $10^{-8}$ | 5.76 ± 1.53 |
| | $10^{-6}$ | 0.40 ± 0.98 |
| 1α,25-Dihydroxy-$\Delta^{16}$-cholecalciferol | $10^{-6}$ | 0.49 ± 0.13 |

Squamous carcinoma cell line (SCC/15) grown for one week in DMEM:F10 with 10% serum plus additives. Number of cells determined for each treatment in triplicate cultures.

From the above results, it can be seen that compounds of formula I induce differentiation of skin cells. Accordingly, compounds of formula I are useful in the treatment of hyperproliferative disorders of the skin such as psoriasis.

The useful activity of compounds of formula I as agents for the treatment of neoplastic diseases can be demonstrated by the following test procedures.

Methods

Tissue culture medium used in these experiments was RPMI-1640 supplemented to 10% v/v with heat-inactivated fetal bovine serum and to an additional 1.6 mM with L-glutamine.

Test compounds were dissolved in sufficient ethanol to yield stock solutions of $1 \times 10^{-2}$ or $1 \times 10^{-3}$ molar. Reduced lighting was used when working with compounds and stock solutions were stored in the dark at −20° in an argon atmosphere. Compounds were diluted in tissue culture medium and added to flasks containing HL-60 cells to achieve the final concentration described in each experiment.

The HL-60 tumor cell line was originally derived from a patient with promyelocytic leukemia and was obtained from the American Type Culture Collection. The cells were maintained in liquid culture by serial passage twice weekly in tissue culture medium. Cells were routinely tested for mycoplasma and were found to be negative. In any experiment, three replicate flasks were incubated without compound (control) or in the presence of varying concentrations of the test compound. Ethanol, used as the vehicle, was kept constant in all dilutions in each experiment and had no effect on cell proliferation, viability or cell differentiation at the concentrations used (→0.1%). After 8 days of incubation at 37° in a humidified atmosphere of 5% $CO_2$ in air, cultures were evaluated for tumor cell proliferation, viability and differentiation.

Quantitation of proliferation was done by enumerating the number of HL-60 cells in each individual flask (3 flasks per experimental point) using an Elzone electronic particle counter. Results are shown as the percent reduction of cell number calculated for each concentration tested according to the formula:

$$1 - \frac{\text{mean number of cells in experimental cultures}}{\text{mean number of cells in control cultures}} \times 100$$

The results are also expressed as the concentration which reduced the cell number by 50% ($ID_{50}$).

Viability of tumor cells was determined by the method of trypan blue dye exclusion. Cells in tissue culture medium were added to an equal volume of 0.4% trypan blue in saline. Cells were scored as viable upon microscopic examination if they excluded dye and as dead if they were stained blue. The viability of cells from experimental cultures was not appreciably different from control cultures indicating that the compounds tested were not toxic to HL-60 cells at concentrations which inhibited proliferation and induced cellular differentiation.

Quantitation of differentiated cells was done by the biochemical method of nitroblue tetrazolium reduction (NBT) reduction. One million HL-60 cells were pooled from replicate cultures, centrifuged at 220×g for 10 minutes, and resuspended in 1 ml of $Ca^{++}$-$Mg^{++}$-deficient phosphate buffered saline (prepared by supplementing $Ca^{++}$-$Mg^{++}$-free phosphate buffered saline (PBS) to 20% v/v with heat-inactivated fetal bovine serum). Nitroblue tetrazolium was dissolved at 0.5 mg per ml in $Ca^{++}$-$Mg^{++}$-free PBS with gentle heating and frequent mixing. A stock solution of 1 mg tetradecanoyl phorbol acetate (TPA) per ml in ethanol, stored at −20°, was diluted 100-fold with $Ca^{++}$-$Mg^{++}$-free PBS to prepare a working solution. The test was done by adding 1 ml of NBT solution and 0.02 ml of the working TPA solution to the HL-60 cells. After mixing, the tubes were incubated in a 37° water bath for 25 minutes then transferred to ice. Undifferentiated and differentiated cells present in any sample were determined microscopically by surveying a minimum of 300 cells per sample. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results are expressed as the percentage of differentiated cells present in any sample as calculated according to the formula:

is useful as an agent in the treatment of neoplastic diseases such as leukemia.

TABLE IV

Anti-proliferative and Differentiation-inducing Effects on HL-60 tumor cells.

| Compound | Conc. ($\times 10^{-8}$M) | % Reduction in cell number | $ID_{50}$ ($\times 10^{-8}$M) | % Differentiated cells | $ED_{50}$ ($\times 10^{-8}$M) |
|---|---|---|---|---|---|
| 1α,25-Dihydroxy-cholecalciferol | 0.01 | 6 | | 3 | |
| | 0.1 | 5 | | 11 | |
| | 1 | 16 | 2 | 19 | 2 |
| | 10 | 66 | | 68 | |
| | 100 | 84 | | 98 | |
| 1α,25-Dihydroxy-$\Delta^{16}$-cholecalciferol | 0.01 | 10 | | 3 | |
| | 0.1 | 33 | | 16 | |
| | 1 | 84 | 0.2 | 92 | 0.2 |
| | 10 | 85 | | 97 | |
| | 100 | 85 | | 98 | |
| 25-Hydroxy-$\Delta^{16}$-cholecalciferol | 0.01 | Not Done | | Not Done | |
| | 0.1 | 10 | | 5 | |
| | 1 | 8 | | 4 | |
| | 10 | 14 | 35 | 6 | 32 |
| | 100 | 82 | | 93 | |
| | 1000 | 95 | | 95 | |
| 1α,25-Dihydroxy-$\Delta^{16},\Delta^{23}$-cholecalciferol | 0.01 | 18 | | 3 | |
| | 0.1 | 20 | | 19 | |
| | 1 | 81 | 0.3 | 92 | 0.3 |
| | 10 | 85 | | 97 | |
| | 100 | 86 | | 99 | |
| 25-Hydroxy-$\Delta^{16},\Delta^{23}$-cholecalciferol | 0.01 | Not Done | | Not Done | |
| | 0.1 | 12 | | 1 | |
| | 1 | 12 | | 2 | |
| | 10 | 17 | 150 | 17 | 200 |
| | 100 | 46 | | 31 | |
| | 1000 | 95 | | 97 | |
| 1α,25-Dihydroxy-$\Delta^{16},\Delta^{23}$-yne-cholecalciferol | 0.01 | 6 | | 9 | |
| | 0.1 | 59 | | 50 | |
| | 1 | 80 | 0.07 | 96 | 0.1 |
| | 10 | 81 | | 98 | |
| 25-Hydroxy-$\Delta^{16},\Delta^{23}$-yne-cholecalciferol | 0.1 | Not Done | | Not Done | |
| | 0.1 | 13 | | 4 | |
| | 1 | 10 | | 12 | |
| | 10 | 8 | 70 | 21 | 70 |
| | 100 | 58 | | 55 | |
| | 1000 | 95 | | 91 | |

$$100 \times \frac{\text{number of formazan positive cells}}{\text{total number of cells counted}}$$

The results are also expressed as the concentration of compound which induced differentiation of 50% of the cells ($ED_{50}$).

Results

The results of these experiments are shown in Table IV and document that each of the compounds tested inhibited the proliferation of HL-60 tumor cells. The anti-proliferative effect of each compound was also dose-dependent and the dose response curves were used to obtain the $ID_{50}$ values shown. Cellular differentiation was also clearly stimulated in a dose-dependent manner by each of the compounds tested. Again, the dose response curves were employed to determine the $ED_{50}$ values shown in Table IV. The compounds did not appreciably reduce the viability of the cells nor was there any impact of the vehicle on cellular proliferation, viability or differentiation.

These data indicate that each of the compounds in question restrained the proliferation of human promyelocytic cells, in vitro, even though they were not toxic to the cells. Furthermore, the cells were seen to differentiate toward a more mature phenotype at the same doses which inhibited proliferation. From these results it can be seen that each of the compounds tested The above test procedures show that compounds of formula I inhibit cell proliferation and induce cell differentiation. Accordingly, the compounds of formula I are useful as agents in the treatment of neoplastic diseases such as leukemia.

In the above tables, 1α,25-dihydroxy-$\Delta^{16}$-cholecalciferol is 1α,25-dihydroxy-16-ene-cholecalciferol;

25-hydroxy-$\Delta^{16}$-cholecalciferol is 25-hydroxy-16-ene-cholecalciferol;

1α,25-dihydroxy-$\Delta^{16},\Delta^{23}$-cholecalciferol is 1α,25-dihydroxy-16,23E-diene-cholecalciferol;

25-hydroxy-$\Delta^{16},\Delta^{23}$-cholecalciferol is 25-hydroxy-16,23E-diene-cholecalciferol;

1α,25-dihydroxy-$\Delta^{16}$-23-yne-cholecalciferol is 1,25-dihydroxy-16-ene-23-yne-cholecalciferol;

25-hydroxy-$\Delta^{16}$-23-yne-cholecalciferol is 25-hydroxy-16-ene-23-yne-cholecalciferol.

The useful activity of compounds of formula I as agents for the treatment of sebaceous gland diseases such as acne or seborrheic dermatitis can be demonstrated by the following test procedures:

Methods

Sebaceous cells are isolated from adult human sebaceous glands, derived from facial skin removed during cosmetic surgery, and cultured on a layer of mouse 3T3 fibroblasts Rheinwald, J. G. and Green H. Serial cultivation of strains of human epidermal keratinocytes: The formation of keratinizing colonies from single cells. Cell 6: 331-334(1975). This method is based on that of Karasek, M. Isolation and characterization of cells from the human sebaceous gland. In Vitro 22: Number 3, Part II, pg. 22a abstract #46(1986) and involves the separation of the epidermal layer from the dermis by an electrokeratome. The dermal tissue is then treated, by enzymatic and mechanical methods, to generate a single cell suspension of sebaceous cells.

The cells are cultured in either Iscove's medium containing 2% human serum, 8% fetal calf serum and 4 ug/ml dexamethasone, or Iscove's medium containing 10% fetal calf serum and 4 ug/ml dexamethasone.

Cells are plated in medium without a compound of the invention and then given the compound in fresh medium 24-48 hours after the initial plating. The cultures are given fresh medium, containing a compound of the invention, every 48 hours. On the day of harvesting, the cultures are rinsed with 0.03% EDTA in PBS, to remove only the 3T3 fibroblasts. The remaining sebocyte colonies are incubated in 0.05% trypsin/0.03% EDTA to create a single cell suspension of sebocytes. The cells are diluted, mixed vigorously to maintain a single cell suspension, and counted in a hemocytometer.

All compounds of the invention are handled in the following manner. Stock solutions are made up as $10^{-2}$M solutions in degassed 100% ethanol and stored at $-20°$ C. in the dark. Solutions are never used after storage of more than a month. During experimental use the solutions, which have been aliquoted, are thawed once and used by diluting directly into complete medium to the appropriate concentration, at $10^{-6}$, $10^{-7}$, $10^{-8}$ and $10^{-9}$M. The compounds tested in the inhibition of proliferation assay for sebaceous cells were:

Compound A: 1α,25-dihydroxycholecalciferol

Compound B: 1α,25-dihydroxy-16-ene-23-yne-cholecalciferol

Compound C: 25-hydroxy-16-ene-23-yne-cholecalciferol

Compound D: 25-hydroxy-16,23E-diene-cholecalciferol

Compound E: 1α,25-dihydroxy-16-ene-cholecalciferol

Results

The compounds were tested for the inhibition of proliferation of sebaceous cells in vitro at the following concentrations: $10^{-6}$, $10^{-7}$, $10^{-8}$ and $10^{-9}$M. 1α,25-dihydroxycholecalciferol, is an agent for reducing the size of sebaceous glands in the ears of the male Syrian hamster. It was included in the test.

The results are summarized in the table as the amount of compound necessary to inhibit the proliferation of the sebaceous cells by 50% as compared to a control. The control was a culture treated with diluent only.

| Inhibition of Human Sebocyte Proliferation In Vitro | |
|---|---|
| Compound | ED$_{50}$ (uM) |
| A | 0.005 |
| B | 0.001 |
| C | 0.1 |
| D | >1 |
| E | 0.001 |

The results demonstrate that the compounds of the invention inhibit human sebocyte proliferation in vitro. Therefore, the compounds of the invention are useful as agents for the treatment of acne.

1α,25-dihydroxycholecalciferol is disclosed in Malloy et al., Page 475, The Journal of Investigative Dermatology, March 1989, Volume 92, Number 3 as an agent for reducing the size of sebaceous glands in the ears of male Syrian hamsters.

Several compounds were evaluated for topical anti-acne activity in the hamster ear sebaceous gland model. For these studies the compounds were dissolved in acetone. Fifty μl of the drug-containing sooution was applied daily (5 days per week) to the dorsal side of the right ear of the hamster. Control hamsters received 50 μl of acetone. The animals were sacrificed after 4 weeks. The ears were removed and processed for histological evaluation. The areas of the sebaceous glands were determined from the cross sections by image analysis. The data are expressed as percent change from control animals.

| Compound | Dose ug/hamster | Change in Hamster Ear Sebaceous Gland Size Cross Section Analysis |
|---|---|---|
| 25-16Δ-23-yne D$_3$ | 0.01 | −8% ns |
| " | 0.10 | −23%*** |
| " | 1.00 | −40%*** |
| " | 10.00 | −64%*** |
| 25-16Δ-23-ene D$_3$ | 0.10 | −16%* |
| " | 1.00 | −16% ns |
| " | 10.00 | −43%*** |

As used in this application, 25-16Δ-23-yne D$_3$ means 25-hydroxy-16-ene-23-yne-cholecalciferol; and 25-16Δ-23-ene D$_3$ means 25-hydroxy-16,23-diene-cholecalciferol.

I. Soft Tissue Calcification Model

The purpose of this test was to evaluate the calcification of soft tissues by the compounds of the invention. Rats were labelled with a single subcutaneous injection of 40 μCi $^{45}$Ca on day one of the study. The compounds were then administered either subcutaneously or topically for four consecutive days. The rats were sacrificed by CO$_2$ inhalation twenty-four hours after the last injection. The hearts and kidneys were removed, placed into glass scintillation vials and digested for 24 hours with 2.0 ml nitric acid. An aliquot (0.2 ml) of the digest was then added to 9.8 ml Aquasol and counted in a scintillation counter.

A calculation ratio has been calculated for the compounds of interest and is determined as follows:

$$\text{Calcification Ratio} = \frac{1.25 \ (OH)_2D_3 \text{ cpm } - \text{ control cpm}}{\text{Compd. cpm } - \text{ control cpm}}$$

The calcification ratio obtained for several Vitamin D analogs, given by the two routes of administration, are as follows:

| Compound | Subcutaneous | Topical |
|---|---|---|
| 1,25 (OH$_2$)D$_3$ | 1 | 1 |
| 1,25-16Δ-23-yneD$_3$ | 47 | <1 |
| 25,-16Δ-23-yneD$_3$ | >1400 | >34 |
| 25-16Δ-23-ene-D$_3$ | >1400 | >34 |

As used in this application 1,25(OH)$_2$D$_3$ means 1α,25-dihydroxycholecalciferol; and 1,25-16Δ-23yneD$_3$ means 1α,25-dihydroxy-16-ene-23-yne-cholecalciferol.

II. Hamster Ear Model

The purpose of this test was to evaluated the effect of compounds of the invention on the sebaceous glands of the hamster ear after oral administration of the compounds. Two hundred μl of a compound of the invention was dissolved in propylene glycol, administered daily (5 days per week) by gavage to male Golden Syrian hamsters. The animals were sacrificed at 4 weeks and the ears were processed for histological evaluation. The area of the sebaceous glands was measured on histologically prepared cross sections of the ear by image analysis. The data obtained from this study is presented below:

| Compound | Dose ug/kg | % Change in Hamster Ear Sebaceous Gland Size Cross Section Analysis |
|---|---|---|
| 25-16Δ-23-yneD$_3$ | 0.05 | −16* |
| " | 0.50 | −23** |
| " | 5.00 | −42*** |
| " | 50.00 | −55*** |
| 25-16Δ-23-eneD$_3$ | 2.50 | −15* |
| " | 5.00 | −22** |
| " | 10.00 | −27*** |
| " | 20.00 | −36*** |

*p <0.05; p <0.01; *p <0.001

The above data demonstrate that certain compounds of the invention are useful as agents in the treatment of sebaceous gland diseases such as acne or seborrheic dermatitis. Moreover, certain compounds of the invention bring about less soft tissue calcification than does 1α,25-dihydroxycholecalciferol. Soft tissue calcification is an undesirable side effect in a compound to be used for treating sebaceous gland diseases.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous lining of the mouth or lower colon.

EXAMPLE 1

Preparation of
[1(R*),3aR*,(3aβ,4α,7aα)]-3a,4,5,6,7,7a-hexahydro-4-hydroxy-β,7a-dimethyl-3H-indene-1-ethanol 4-methyl-benzenesulfonate A mixture of 3.24 g (15.4 mmol) of [1(R*),3aR*-(3aβ, 4α,7aα)]-3a,4,5,6,7,7a-hexahydro-4-hydroxy-β, 7a-dimethyl-3H-indene-1-ethanol, 30 ml of dry pyridine, and 3.51 g (18.4 mmol) of p-toluenesulfonyl chloride was stirred at 0° C. for 18 hr. The mixture was quenched with ice chips. After dilution with water, the mixture was extracted with methylene chloride. The organic phase was washed with 1N aqueous H$_2$SO$_4$, saturated aqueous NaHCO$_3$, dried (Na$_2$SO$_4$) and evaporated to dryness. The residue was chromatographed on silica gel (40–63μ) using ethyl acetate-hexane (1:1.5) as an eluant to afford 4.61 g (82%) of [1(R*),3aR*-(3aβ,-4α,7aα)]-3a,4,5,6,7,7a-hexahydro-4-hydroxy-β,7a-dimethyl-3H-indene-1-ethanol 4-methyl-benzenesulfonate as a glass: [α]$_D^{21}$+31.9° (c 0.53, CHCl$_3$); IR (CHCl$_3$) 3620, 1358, 1175 cm$^{-1}$; $^1$H NMR (CDCl$_3$) & 0.95 (s, 3H), 1.00 (d, J=8 Hz, 3 H), 2.20 (m, 1 H), 2.41 (m, 1 H) 2.45 (s, 3 H), 3.85–4.35 (m, 2 H), 4.18 (br s, 1 H), 5.27 (br s, 1 H) 7.36 (d, J=8 Hz, 2 H), 7.80 (d, J=8 Hz, 2 H); MS m/e 364 (M+).

EXAMPLE 2

Preparation of
[1(R*),3aR*-(3aβ,4α,7aα)]-3a,4,5,6,7,7a-hexahydro-4-hydroxy-β,7a-dimethyl-3H-indene-1-propanenitrile To a solution of 4.61 g (12.6 mmol) of [1(R*),3aR*-(3aβ,4α,7aα)]-3a,4,5,6,7,7a-hexahydro-4-hydroxy-β,7a-dimethyl-3H-indene-1-ethanol 4-methyl-benzenesulfonate in 22 ml of dry dimethyl sulfoxide was added 1.10 g (22.4 mmol) of sodium cyanide and the mixture was heated at 90° C. for 2 hours. After cooling to room temperature, the mixture was pumped to remove most of the solvent then diluted with water. The mixture was extracted with ether. The organic phase was washed with saturated brine, dried (Na$_2$SO$_4$) and evaporated to dryness. The residue was chromatographed on silica gel (40–63μ) using methylene chloride-hexaneethyl acetate (86:7:7) as an eluant to give 2.52 g (91%) of [1(R*),3aR*-(3aβ,4α,7aα)]-3a,4,5,6,7,7a-hexahydro-4-hydroxy-β,7a-dimethyl-3H-indene-1-propanenitrile as a glass: [α]$_D^{21}$+29.2° (c 0.65, CHCl$_3$); IR (CHCl$_3$) 3620, 2245 cm$^{-1}$; $^1$H NMR (CDCl$_3$) & 1.10 (s, 3 H), 1.19 (d, J=8Hz, 3 H), 2.26-2.60 (m, 4 H), 4.21 (br s, 1 H), 5.48 (br s, 1 H) MS m/e 219 (M+).

EXAMPLE 3

Preparation of
[1(R*),3aR*-(3aβ,4α,7aα)]-3a,4,5,6,7,7a-hexahydro-4-hydroxy-β,7a-dimethyl-3H-indene-1-propanal To a mixture of 6.85 ml (6.85 mmol) of diisobutylaluminum hydride in hexane (1M) and 5.2 ml of dry methylene chloride at −6° C. was added a solution of 0.430 g (1.96 mmol) of [1(R*),3aR*-(3aβ,4α,7aα)]-3a,4,5,6,7, 7a-hexahydro-4-hydroxy-β,7a-dimethyl-3H-indene-1-propanenitrile in 10 ml of dry methylene chloride. The mixture was stirred at −6° C. for 55 minutes. After quenching with saturated ammonium chloride solution, the mixture was hydrolyzed with 3N HCl-ether (2:1 by volume) The aqueous layer was withdrawn and extracted with ether. The combined organic layers were washed with saturated brine, dried (MgSO$_4$) and evaporated to dryness. The residue was chromatographed on silica gel (40–63μ) using ethyl acetate-hexane (1:2) as an eluant to afford 260 mg (60%) of [1R*),3aR*-(3aβ,4α,7aα)]-3a,4,5,6,7,7a-hexahydro-4-hydroxy-β,7a-dimethyl-3H-indene-1-propanal as a glass: [α]$_D^{22}$+43.1° (c 0.32, CHCl$_3$); IR (CHCl$_3$) 3620, 3580, 2725, 1720 cm$^{-1}$; $^1$H NMR (CDCl$_3$) & 1.07 (s, 3 H), 1.08 (d, J=8 Hz, 3 H), 2.25 (m,1H), 2.46 (m, 1 H), 2.55-2.80 (m, 2 H), 4.19 (br s, 1 H), 5.35 (br s, 1 H), 9.68 (s, 1 H).

EXAMPLE 4

Preparation of
[1(R*),3aR*-(3aβ,4α,7aα)]-1-(4,4-dibromo-1-methyl-3-butenyl)-3a,4,5,6,7,7a-hexahydro-7a-methyl-3H-indene-4-ol A mixture of 1.77 g (6.75 mmol) of triphenylphosphine, 2.23 g (6.72 mmol) of carbon tetrabromide, 441 mg (6.75 m atom) of Zn dust, and 23 ml of methylene chloride was stirred at 25° C. for 31 hours. To this mixture was added a solution of 0.430 g (1.93 mmol) of [1(R*),3aR*-(3aβ,4α, 7aα)]-3a,4,5,6,7,7a-hexahydro-4-hydroxy-β,7a-dimethyl-3H-indene-1-propanal in 38 ml of dry methylene chloride and the mixture was stirred at room temperature for 18 hours. The mixture was diluted with pentane and insoluble material was filtered. The insoluble fraction was dissolved in methylene chloride and the solution was again diluted with pentane. After filtration, the combined filtrates were evaporated to dryness. The residue was purified by chromatography on 40–63μ silica gel (eluted with 1:4 ethyl acetate-hexane) to give 0.490 g (67%) of [1(R*),3aR*-(3aβ,4α,-7aα)]-1-(4,4-dibromo-1-methyl-3-butenyl)-3a,4,5,6,7,7a-hexahydro-7a-methyl-3H-indene-4-ol as a glass: [α]$_D^{22}$+14.4° (c 0.55, CHCl$_3$); IR (CHCl$_3$), 3620, 1606, 1618 cm$^{-1}$; $^1$H NMR (CDCl$_3$) δ1.03 (d, J=8 Hz, 3 H), 1.05 (s, 3 H), 2.14-2.36 (m, 4 H), 4.17 (br s, 1 H), 5.36 (br s, 1 H), 6.33 (m, 1 H); MS m/e 376 (M+)

EXAMPLE 5

Preparation of
[1(R*),3aR*-(3aβ,4α,7aα)]-3a,4,5,6,7,7a-hexahydro-7a-methyl-1-(1-methyl-3-butynyl)-3H-inden-4-ol To a solution of 0.680 g (1.80 mmol) of [1(R*),3aR*-(3aβ,4α,7aα)]-1-(4,4-dibromo-1-methyl-3-butenyl)-3a,4,5,6,7,7a-hexahydro-7a-methyl-3H-inden-4-ol in 31 ml of dry tetrahydrofuran at −75° C. was added 3.77 ml (6.03 mmol) of 1.6M solution of butyllithium in hexane dropwise. The 10 mixture was then stirred at −75° C. for 1 hour and at 25° C. for 1 hour. The reaction was quenched by addition of saturated brine. The mixture was diluted with saturated aqueous NaHCO$_3$ and extracted with ether. The organic phase was washed with saturated brine, dried (MgSO$_4$), and evaporated to dryness. The residue was chromatographed on silica gel (40–63μ) using ethyl acetate-hexane (1:4) to afford 0.350 g (89%) of [1(R*),3aR*-(3aβ,4α,7aα)]-3a, 4, 5,6,7,7a-hexahydro-7a-methyl-1-(1-methyl-3-butynyl)-3H-inden-4-ol as an oil: [α]$_D^{22}$+30.7° (c 0.42, CHCl$_3$); IR (CHCl$_3$) 3620, 3305, 1618 cm$^{-1}$; H$^1$NMR (CDCl$_3$) δ1.07 (s, 3 H), 1.12 (d, J=8 Hz, 3 H), 1.93 (s, 1 H), 2.16-2.40 (m, 4 H) 4.17 (br s, 1 H), 5.40 (br s, 1 H); MS m/e 218 (M+).

EXAMPLE 6

Preparation of [1(R*),3aR*-(3aβ,4α,7aα)]-3a,4,5,6,7, 7a-hexahydro-7a-methyl-1-(1-methyl-3-butynyl)-4-[(trimethylsilyl)oxy]-3H-indene To a solution of 1.29 g (5.91 mmol) of [1(R*),3aR*-(3aβ,4α,7aα)]-3a,4,5,6,7,7a-hexahydro-7a-methyl-1-(1-methyl-3-butynyl)-3H-inden-4-ol in 80 ml of dry methylene chloride was added 3.59 g (25.6 mmol) of 1-(trimethylsilyl)imidazole. The mixture was then stirred at 25° C. for 3 hours. The mixture was quenched by adding 40 ml of water and stirred at 25° for 20 minutes. The mixture was extracted with ethyl acetate. The organic phase was washed with water, saturated brine, dried (Na$_2$SO$_4$), and evaporated to dryness. The residue was purified by chromatography on 40–63μ silica gel using ethyl acetate-hexane (1:15) to give 1.70 g (99%) of [1(R*),3aR*-(3aβ,4α,7aα)]-3a, 4,5,6,7,7a-hexahydro-7a-methyl-1-(1-methyl-3-butynyl)-4-[(trimethylsilyl)oxy]-3H-indene as an oil: [α]$_D^{20}$+39.7° (0.30, CHCl$_3$); IR (CHCl$_3$) 3305, 2115, 842 cm$^{-1}$; $^1$H NMR (CDCl$_3$) δ 0.07 (s, 9 H), 1.01 (s, 3 H), 1.11 (d, J=8 Hz, 3 H), 1.95 (s, 1 H), 2.12-2.38 (m, 4 H)4.07 (br, s, 1 H), 5.34 (s, 1 H).

EXAMPLE 7

Preparation of [1(R*),3aR*-(3aβ,4α,7aα)]-6-(3a,4,5,6, 7,7a-hexahydro-7a-methyl-4-[(trimethylsilyl)oxy]-3H-inden-1-yl)-2-methyl-3-heptyn-1-ol To a solution Of 1.70 g (5.84 mmol) of [1(R*),3aR*-(3aβ,4α,7aα)]-3a,4,5,6,7,7a-hexahydro-7a-methyl-1-(1-methyl-3-butynyl)-4-[(trimethylsilyl)oxy]-3H-indene in 48 ml of dry tetrahydrofuran at −75° C. was added 6.01 ml (9.63 mmol) of 1.6M butyllithium in hexane dropwise. After stirring for 40 minutes at −75° C., 3.05 ml (41.5 mmol) of dry acetone was added and the mixture stirred at −75° C. for 20 minutes then at 25° C. for 1 hour and 15 minutes. The reaction was quenched at 0° C. by addition of 40 ml of a 1:1 mixture of 2M aqueous KHCO$_3$ and 1M aqueous potassium sodium tartrate. The mixture was stirred at 25° C. for 20 minutes then extracted with ethyl acetate. The organic phase was washed with saturated brine, dried ($Na_2SO_4$), and evaporated to dryness. The residue was chromatographed on silica gel (40–63μ) using ethyl acetate-hexane (1:5) to give 1.62 g (89%) of [1(R*),3aR*-(3aβ,4α,7aα)]-6-(3a,4,5,6,7,7a-hexahydro-7a-methyl 4-[(trimethylsilyl)oxy]-3H-inden-1-yl)-2-methyl-3-heptyn-1-ol as an oil: $[α]_D^{20}+39.7°$ (c 0.30, $CHCl_3$); IR ($CHCl_3$) 3600, 2230, 842 cm$^{-1}$; $^1$H NMR ($CDCl_3$) δ0.07 (s, 9 H), 1.01 (s, 3 H), 1.07 (d, J=8 Hz, 3 H), 1.50 (s, 6 H), 2.10–2.40 (m, 4 H), 4.08 (br s, 1 H), 5.22 (br s, 1 H); MS m/e 348 (M+).

EXAMPLE 8

Preparation of [1(R*),3aR*-(3aβ,4α,7aα)]-3a,4,5,6,7,7a-hexahydro-1-(1,5-dimethyl-5-hydroxy-3-hexynyl)-7a-methyl-3H-inden-4-ol To a solution of 1.62 g (5.17 mmol) of [1(R*),3aR*-(3aβ,4α,7aα)]-6-(3a,4,5,6,7,7a-hexahydro-7a-methyl-4-[(trimethyl-silyl)oxy]-3H-inden-1-yl)-2-methyl-3-heptyn-1-ol in 53 ml of dry tetrahydrofuran was added 15.5 ml (15.5 mmol) of 1M tetrabutylammonium fluoride in tetrahydrofuran. The mixture was stirred at room temperature for 50 minutes. After dilution with half saturated aqueous $NaHCO_3$, the mixture was evaporated to remove most of the solvent and extracted with ethyl acetate. The organic phase was washed with half saturated brine, dried ($Na_2SO_4$), and evaporated to dryness. The residue was chromatographed on silica gel (40–63μ) using ethyl acetate-hexane (1:1) to give 1.17 g (82%) of [1(R*),3aR*-(3aβ,4α,7aα)]-3a,4,5,6,7,7a-hexahydro-1-(1,5-dimethyl-5-hydroxy-3-hexynyl)-7a-methyl-3H-inden-4-ol as a solid: m.p 105°–107°; $[α]_D^{24}+23.4°$ (c 0.32, $CHCl_3$); IR ($CHCl_3$) 3600, 2230, cm$^{-1}$; δ1.07 (s, 3 H), 1.08 (d, J=8 Hz, 3 H), 1.48 (s, 6 H), 2.19–2.43 (m, 4 H) 4.19 (br s, 1 H), 5.38 (br s, 1 H); MS m/e 276 (M+).

EXAMPLE 9

Preparation of [1(R*),3aR*-(3aβ,7aα)]-3,3a,5,6,7,7a-hexahydro-1-(5-hydroxy-1,5-dimethyl-3-hexynyl)-7a-methyl-4H-inden-4-one To a solution of 0.720 g (2.60 mmol) of [1(R*),3aR*-(3aβ,4α,7aα)]-3a,4,5,6,7,7a-hexahydro-1-(1,5-dimethyl-5-hydroxy-3-hexynyl)-7a-methyl-3H-inden-4-ol in 44 ml of dry methylene chloride was added 1.59 g (19.4 mmol) of anhydrous sodium acetate and 3.18 g (10.5 mmol) of 2,2'-bipyridinium chlorochromate The mixture was stirred at 25° C. for 2 hours. Additional 1.59 g (5.27 mmol) of 2,2'-bipyridinium chlorochromate was then added and the stirring continued for an additional 2 hours. After this time, 6 ml of 2-propanol was introduced and 15 minutes later, the mixture was diluted with water and extracted with ether-ethyl acetate (1:1). The organic phase was washed with water, 1N aqueous $H_2SO_4$, saturated aqueous $NaHCO_3$ and saturated brine. After drying ($Na_2SO_4$), the solution was evaporated and the residue chromatographed on silica gel (40–63μ) using ethyl acetate-hexane (1:1) to give 0.560 g (78%) of [1(R*),3aR*-(3aβ, 7aα)]-3,3a,5,6, 7,7a-hexahydro-1-(5-hydroxy-1,5-dimethyl-3-hexynyl)-7a-methyl-4H-inden-4-one as a glass: $[α]_D^{20}+35.3°$ (c 0.36, $CHCl_3$); IR ($CHCl_3$) 3600, 2225, 1709 cm$^{-1}$; $^1$H NMR ($CDCl_3$) δ0.84 (s, 3 H), 1.15 (d, J=8 Hz, 3 H), 1.46 (s, 6 H), 2.44 (m, 1 H), 2.85 (m 1 H), 5.36 (br s, 1 H); MS m/e 274 (M+).

EXAMPLE 10

Preparation of [1(R*),3aR*-(3aβ,7aα)]-3,3a,5,6,7,7a-hexahydro-1-(1,5-dimethyl-5-[(trimethylsilyl)oxy]-3-hexynyl) 7a-methyl-4H-inden-4-one To a solution of 0.552 g (2.01 mmol) of [1(R*),3aR*-(3aβ,7aα)]-3,3a,5,6,7,7a-hexahydro-1-(5-hydroxy-1,5-dimethyl-3-hexynyl)-7a-methyl-4H-inden-4-one in 70 ml of dry methylene chloride was added 2.00 g (14.2 mmol) of 1-(trimethylsilyl)imidazole The mixture was then stirred at 25° C. for 17 hours. The mixture was quenched by adding 22 ml of water and stirred at 25° C. for 20 minutes. The mixture was extracted with ethyl acetate. The organic phase was washed with water, saturated brine, dried ($Na_2SO_4$), and evaporated to dryness. The residue was chromatographed on silica gel (40–63μ) using ethyl acetate-hexane (1:4) to give 0.693 g (99%) of [1(R*),3aR*-(3aβ,7aα)]-3,3a,5, 6,7,7a-hexahydro-1-(1,5-dimethyl-5-[(trimethylsilyl)oxy]-3-hexynyl)-7a-methyl-4H-inden-4-one as a glass: $[α]_D^{20}+29.5°$ (c 0.20, $CHCl_3$); IR ($CHCl_3$) 1710, 842 cm$^{-1}$; $^1$H NMR ($CDCl_3$) δ0.16 (s, 9 H), 0.84 (s, 3 H) 1.14 (d, J=8 Hz, 3 H), 1.43 (s, 6 H), 1.77 (m, 1 H) 1.91 (m, 1 H), 2.84 (m, 1 H) 5.34 (br s, 1 H); MS m/e 346 (M+).

EXAMPLE 11

Preparation of (1α,3β,5Z,7E)-1,3-bis[[1,1-dimethylethyl)dimethylsilyl]oxy-25-[(trimethylsilyl)oxy]-9,10-secocholesta-5,7,10(19),16-tetraene-3-yne To a solution of 2.00 g (3.20 mmol) of [3S-(1Z,3α,5β)]-[2-[3,5-bis[[(1,1-dimethyl)dimethylsilyl]oxy]-2-methylenecyclohexylidene]ethyl]diphenylphosphine oxide in 45 ml of dry tetrahydrofuran at −75° C. was added dropwise 1.87 ml (2.99 mmol) of 1.6M butyllithium in hexane. After stirring for 6 minutes a solution of 0.693 g (2.00 mmol) of [1(R*),3aR*-(3aβ,7aα)]-3,3a,5,6,7,7a-hexahydro-1-(1,5-dimethyl-5-[(trimethylsilyl)oxy]-3-hexynyl)-7a-methyl-4H-inden-4-one in 26 ml of dry tetrahydrofuran was added dropwise The mixture was stirred at −75° C. for 1 hour and 10 minutes and quenched by addition of 1:1 mixture of 1M aqueous potassium sodium tartrate and 2M aqueous $KHCO_3$. The mixture was extracted with ethyl acetate The organic phase was washed with saturated brine, dried ($Na_2SO_4$), and evaporated to dryness. The residue was chromatographed on silica gel (40–63μ) using ethyl acetate-hexane (1:15) to give 1.23 g (87%) of (1α,3β,5Z,7E)-1,3-bis[[1,1-dimethylethyl)dimethylsilyl]-oxy-25-[(trimethylsilyl)oxy]-9,10-secocholesta-5,7,10(19),16-tetraene-3-yne as a glass: $[α]_D^{23}+47.1°$ (c 0.21, $CHCl_3$); IR ($CHCl_3$) 2213, 838 cm$^{-1}$; $^1$H NMR ($CDCl_3$) δ0.05 (s, 6 H), 0.06 (s, 6 H), 0.16 (s, 9 H), 0.70 (s, 3 H), 0.84 (s, 9 H), 0.87 (s, 9 H), 1.11 (d, J=8 Hz, 3 H), 1.43 (s, 6 H), 2.45 (m 1 H), 2.81 (m, 1 H), 4.20 (br s, 1 H), 4.38 (br s, 1 H), 4.89 (s, 1 H), 5.36 (s, 1 H), 6.09 (d, J=12 Hz, 1 H), 6.24 (d, J=12 Hz, 1 H); MS m/e 710 (M+).

EXAMPLE 12

Preparation of 1α,25-dihydroxy-16-ene-23-yne-cholecalciferol

To a solution of 0.228 g (0.321 mmol) of (1α,3β,5Z,7E)-1,3-bis[[1,1-dimethylethyl)dimethylsilyl]oxy]-25-[(trimethylsilyl)oxy]-9,10-secocholesta-5,7,10(19),16-tetraene-3-yne in 11 ml of tetrahydrofuran was added 1.92 ml (1.92 mmol) of 1M tetrabutylammonium fluoride in tetrahydrofuran. The mixture was stirred at room temperature for 16 hours. After dilution with water, the mixture was extracted with ethyl acetate. The organic phase was washed with half saturated brine, saturated brine, dried ($Na_2SO_4$), and evaporated to dryness. The residue was purified by chromatography on silica gel (40–63μ) using ethyl acetate-hexane (3:1) to afford 0.126 g (96%) of 1,25-dihydroxy-16-ene-23-yne-cholecalciferol as a glass: $[\alpha]_D^{21}$+21.5° (C 0.20, MeOH); IR ($CHCl_3$) 3605, 1648, 1622 $cm^{-1}$; $^1H$ NMR ($CDCl_3$) δ0.72 (s, 3 H), 1.12 (d, J=8 Hz, 3 H), 2.71 (m 1 H), 2.83 (m, 1 H), 4.25 (br s, 1 H), 4.46 (br s, 1 H), 5.10 (br s, 1 H), 5.42 (br s, 1 H), 5.48 (br s, 1 H), 6.19 (d, J=12 Hz, 1 H), 6.46 (d, J=12 Hz, 1 H); MS m/e 410 (M+); UV max (EtOH) 263 nm.

EXAMPLE 13

Preparation of (3β,5Z,7E)-3-[[1,1-dimethylethyl)dimethylsilyl]oxy]-25-[(trimethylsilyl)oxy]-9,10-secocholesta-5,7,10 (19),16-tetraene-23-yne To a solution of 0.343 g (0.758 mmol) of [5S-(1Z)]-[2-[5-[[(1,1-dimethylethyl)dimethylsilyl]oxy]-2-methylenecyclohexylidene]ethyl diphenylphosphine oxide in 8.5 ml of dry tetrahydrofuran at −75° C. was added dropwise 0.466 ml (0.746 mmol) of 1.6M butyllithium in hexane. After stirring for 6 minutes a solution of 0.186 g (0.537 mmol) of [1(R*),3aR*-(3aβ,7aα)]-3,3a,5,6,7,7a-hexahydro-1-(1,5-dimethyl-5-[(trimethylsilyl)oxy]-3-hexynyl)-7a-methyl-4H-inden-4-one in 9 ml of dry tetrahydrofuran was added dropwise. The mixture was stirred at −75° C. for 1 hour and quenched by addition of 1:1 mixture of 1M aqueous potassium sodium tartrate and 2M aqueous $KHCO_3$. The mixture was extracted with ethyl acetate. The organic phase was washed with saturated brine, dried ($Na_2SO_4$), and evaporated to dryness. The residue was chromatographed on silica gel (40–63μ) using ethyl acetate-hexane (1:15) to give 0.250 g (80%) of (3β,5Z,7E)-3-[[1,1-dimethylethyl)-dimethylsilyl]oxy]-25-[(trimethylsilyl)oxy]-9,10-secocholesta-5,7,10(19), 16-tetraene-23-yne as a glass: $^1H$ NMR ($CDCl_3$) δ0.06 (s, 6 H), 0.17 (s, 9 H), 0.71 (s, 3 H), 0.88 (s, 9 H) 1.12 (d, J=8 Hz, 3 H), 1.43 (s, 6 H), 2.81 (br d, 1 H), 3.81 (br s, 1 H), 4.79 (s, 1 H), 5.01 (s, 1 H), 5.38 (br s, 1 H), 6.07 (d, J=12 Hz, 1 H), 6.15 (d, J=12 Hz, 1 H); MS m/e 580 (M+).

EXAMPLE 14

Preparation of 25-hydroxy-16-ene-23-yne-cholecalciferol

To a solution of 0.248 g (0.427 mmol) of (3β,5Z,7E)-3-[[1,1-dimethylethyl)dimethylsilyl]oxy]-25-[(trimethylsilyl) oxy]-9,10-secocholesta-5,7,10(19),16-tetraene-23-yne in 12 ml of dry tetrahydrofuran was added 2.57 ml (2.57 mmol) of 1M tetrabutylammonium fluoride in tetrahydrofuran. The mixture was stirred at room temperature for 16 hours. After dilution with water, the mixture was extracted with ethyl acetate. The organic phase was washed with half saturated brine, saturated brine, dried ($Na_2SO_4$), and evaporated to dryness. The residue was purified by chromatography on silica gel (40–63μ) using ethyl acetate-hexane (1:1) to afford 0.153 g (91%) of 25-hydroxy-16-ene-23-ynecholecalciferol as a glass: $[\alpha]_D^{21}$+99.6° (c 0.25, MeOH); IR ($CHCl_3$) 3395, 1645, $cm^{-1}$; $^1H$ NMR ($CDCl_3$) δ0.74 (s, 3 H). 1.14 (d, J=8 Hz, 3 H), 2.60 (m, 1 H), 2.83 (m, 1 H), 3.98 (br s, 1 H), 4.85 (s, 1 H), 5.07 (s, 1 H), 5.40 (s, 1 H), 6.12 (d, J=12 Hz, 1 H), 6.23 (d, J=12 Hz, 1 H); MS m/e 394 (M+); UV max (EtOH) 263 nm.

EXAMPLE 15

Preparation of [1(R*),1(3E),3aβ,4α,7aα)]-(3a,4,5,6,7, 7a-hexahydro-1-(5-hydroxy-1,5-dimethyl-3-hexenyl)-7a-methyl-1H-inden-4-ol To a mixture of 0.146 g (3.85 mmol) of lithium aluminum hydride 0.211 g (3.91 mmol) of sodium methoxide, and 6.5 ml of dry tetrahydrofuran at 0° C. was added a solution of 0.180 g (0.651 mmol) of [1(R*),3aR*-(3aβ,-4α,7aα)]-(3a, 4,5,6,7,7a-hexahydro-1-(1,5-dimethyl-5-hydroxy-3-hexynyl)-7a-methyl-3H-inden-4-ol in 13 ml of dry tetrahydrofuran dropwise. The mixture was heated at reflux (ca. 68° C.) for 16 hours, and recooled at 0° C. After dilution with 13 ml of dry ether, the mixture was quenched with the dropwise addition of 0.30 ml of water and 0.26 ml of 10% aqueous NaOH. The mixture was stirred at room temperature for 1 hour and filtered. The solids were triturated with ether and filtered. The combined filtrates were evaporated to dryness and chromatographed on 40–63μ silica gel using ethyl acetate-hexane (1:2) to give 0.179 g (99%) of [1(R*),1(3E),3aβ,4α,7aα)]-(3a,4,5,6,7,7a-hexahydro-1-(5-hydroxy-1,5-dimethyl-3-hexenyl)-7a-methyl-1H-inden-4-ol as a glass: $[\alpha]_D^{21}$+11.5° (c 0.33, $CHCl_3$); IR ($CHCl_3$) 3605 $cm^{-1}$; $^1H$ NMR ($CDCl_3$) δ0.98 (d, J=8 Hz, 3 H), 1.03 (s, 3 H), 1.30 (s, 6 H), 4.18 (br s, 1 H), 5.32 (s, 1 H), 4.47–4.68 (m, 2 H); MS m/e 278 (M+).

EXAMPLE 16

Preparation of [1(R*),1(3E),(3aβ,7aα)]-3,3a,5,6,7,7a-hexahydro-1-(5-hydroxy-1,5-dimethyl-3-hexenyl)-7a-methyl-4H-inden-4-one To a solution of 0.120 g (0.431 mmol) of [1(R*),1(3E), (3aβ,4α,7aα)]-3a,4,5,6,7,7a-hexahydro-1-(5-hydroxy-1,5-dimethyl-3-hexenyl)-7a-methyl-1H-inden-4-ol in 10 ml of dry methylene chloride was added 0.500 g (1.30 mmol) of pyridinium dichromate (98%) and 25 mg of pyridinium p-toluenesulfonate. The mixture was stirred at 25° C. for 2 hours and 15 minutes. After addition of 40 ml of ether, the mixture was stirred at 25° C. for 5 minutes and filtered. The solids were triturated with ether and filtered. The combined filtrates were washed with saturated aqueous $CuSO_4$, water, half saturated aqueous $NaHCO_3$, and saturated brine. The organic phase was dried ($Na_2SO_4$) and evaporated to dryness. The residue was chromatographed on silica gel (40–63μ) using 35% ethyl acetate-hexane to give 90 mg (76%) of [1(R*),1(3E),(3aβ,7aα)]-3,3a,5,6, 7,7a-hexahydro-1-(5-hydroxy-1,5-dimethyl-3-hexenyl)-7a-methyl-4H-inden-4-one as a glass: $[\alpha]_D^{25}$+30.6° (c 0.17, $CHCl_3$); IR ($CHCl_3$) 3600, 1708 $cm^{-1}$; $^1H$ NMR ($CDCl_3$) δ 0.79 (s, 3 H), 1.02 (d, J=8 Hz, 3 H), 1.28 (s, 6 H), 2.42 (m, 1 H), 2.83 (m, 1 H), 5.23 (s, 1 H), 5.40–5.57 (m, 2 H); MS m/e 276 (M+).

EXAMPLE 17

Preparation of [1(R*),1(3E),(3aβ,7aα)]-3,3a,5,6,7,7a-hexahydro-1-(1,5-dimethyl-5-[(trimethylsilyl)oxy1-3-hexenyl)-7a-methyl-4H-inden-4-one To a solution of 0.099 g (0.358 mmol) of [1(R*),1(3E), (3aβ,7aα)]-3,3a,5,6,7,7a-hexahydro-1-(5-hydroxy-1,5-dimethyl-3-hexenyl)-7a-methyl-4H-inden-4-one in 14 ml of dry methylene chloride was added 0.356 g (2.54 mmol) of 1-trimethylsilyl)-imidazole. The mixture was then stirred at 25° C. for 4 hours. The mixture was quenched by adding 4 ml of water and stirred at 25° C. for 20 minutes. The mixture was extracted with ethyl acetate. The organic phase was washed with saturated brine, dried (Na$_2$SO$_4$) and evaporated to dryness. The residue was chromatographed on silica gel (40–63μ) using ethyl acetate-hexane (1:4) to give 0.111 g (89%) of [1(R*),1(3E),(3aβ,7aα)]-3,3a,5, 6,7,7a-hexahydro-1-(1,5-dimethyl-5-[(trimethylsilyl)oxy]-3-hexenyl)-7a-methyl-4H-inden-4-one as a glass: $[α]_D^{24}+26.4°$ (c 0.22, CHCl$_3$); IR (CHCl$_3$) 1708, 840 cm$^{-1}$; $^1$H NMR (CDCl$_3$ δ0.06 (s, 3 H), 0.75 (s, 3 H), 1.02 (d, J= 8 Hz, 3 H), 1.26 (s, 6 H), 2.50 (m, 1 H), 2.92 (m, 1 H), 5.26 (s, 1 H), 5.32–5.54 (m, 2 H); MS m/e 348 (M+).

EXAMPLE 18

Preparation of (1α,3β,5Z,7E,23)-1,3-bis[[(1,1-dimethylethyl)dimethylsilyl]oxy]-25-[(trimethylsilyl)oxy]-9,10-secocholesta-5,7,10(19), 16,23-pentane To a solution of 0.265 g (0.424 mmol) of [3S-(1Z,3α, 5β)]-[2-[3,5-bis[[(1,1-dimethyl)dimethylsilyl]oxy]-2-methyleneycyclohexylidene]ethyl]diphenylphosphine oxide in 6 ml of dry tetrahydrofuran at −75° C. was added dropwise 0.250 ml (0.400 mmol) of 1.6M butyllithium in hexane. After stirring for 6 minutes a solution of 0.095 g (0.27 mmol) of [1(R*),1(3E),(3aβ,7aα)]-3,3a,5,6,7,7a-hexahydro-1-(1,5-dimethyl-5-[(trimethylsilyl)oxy]-3-hexenyl)-7a-methyl-4H-inden-4-one in 3.6 ml of dry tetrahydrofuran was added dropwise. The mixture was stirred at −75° C. for 1 hour and quenched by addition of 1:1 mixture of 1M aqueous potassium sodium tartrate and 2M aqueous KHCO$_3$. The mixture was extracted with ethyl acetate. The organic phase was washed with saturated brine, dried (Na$_2$SO$_4$) and evaporated to dryness. The residue was chromatographed on silica gel (40–63μ) using ethyl acetate-hexane (1:15) to give 0.162 g (83%) of (1β3α,5Z,7E,23E)-1,3-bis[[(1,1-dimethylethyl)dimethylsilyl]oxy]-25-[(trimethylsilyl)oxy]-9,10-secocholesta-5,7,10(19),16,23-pentane as a glass: $^1$H NMR (CDCl$_3$) δ0.07 (s, 12 H), 0.10 (s, 9 H) 0.67 (s, 3 H), 0.88 (s, 18 H), 1.28 (s, 6 H), 2.36 (m, 1 H), 2.47 (m,1 H), 2.82 (m, 1 H), 4.20 (m, 1 H), 4.39 (br s, 1 H), 4.90 (s, 1 H), 5.18 (s, 1 H), 5.31 (s, 1 H), 5.36–5.60 (m, 2 H), 5.10 (d, J=12 Hz, 1 H), 5.25 (d, J=12 Hz, 1 H); MS m/e 712 (M+).

EXAMPLE 19

Preparation of 1,25-dihydroxy-16,23E-diene-cholecalciferol

To a solution of 0.159 g (0.223 mmol) of (1α,3β,5Z, 7E,23E)-1,3-bis[[(1,1-dimethylethyl)dimethylsilyl]oxy]-25-[(trimethylsilyl)oxy]-9,10-secocholesta-5,7,10(19),16,23-pentane in 7.7 ml of tetrahydrofuran was added 1.34 ml (1.34 mmol) of 1M tetrabutylammonium fluoride in tetrahydrofuran. The mixture was stirred at room temperature for 15 hours. After dilution with water, the mixture was extracted with ethyl acetate. The organic phase was washed with half saturated brine, saturated brine, dried (Na$_2$SO$_4$) and evaporated to dryness. The residue was purified by chromatography on silica gel (40–63μ) using ethyl acetate-hexane (5:1) to afford 0.077 g (84%) of 1,25-dihydroxy-16,23E-diene-cholecalciferol as a glass: $[α]_D^{24}+46.5°$ (c 0.20, MeOH); IR (CHCl$_3$) 3605, 1645, 1638 cm$^{-1}$; $^1$H NMR (CDCl$_3$) δ0.68 (s, 3 H), 1.01 (d, J=8 Hz, 3 H), 1.29 (s, 6 H), 2.59 (m, 1 H), 2.80 (m, 1 H), 4.22 (br s, 1 H), 4.43 (br s, 1 H), 5.00 (s, 1 H), 5.29 (s, 1 H), 5.31 (s, 1 H), 5.40–5.56 (m, 2 H), 6.08 (d, J=12 Hz, 1 H), 6.36 (d, J=12 Hz, 1 H); MS m/e 412 (M+); UV max (EtOH) 263 nm.

EXAMPLE 20

Preparation of (3β5Z,7E,23E)-3-[[(1,1-dimethylethyl)dimethylsilyl]oxy]-25-[(trimethylsilyl)oxy]-9,10-secocholesta-5,7,10(19),16,23-pentane To a solution of 0.225 g (0.497 mmol) of [5S-(1Z)]-[2-[5-[[(1,1-dimethylethyl)dimethylsilyl]oxy]-2-methylenecyclohexylidene]ethyl]diphenylphosphine oxide in 5.6 ml of dry tetrahydrofuran at −75° C. was added dropwise 0.296 ml (0.474 mmol) of 1.6M butyllithium in hexane. After stirring for 6 minutes, a solution of 0.110 g (0.316 mmol) of [1(R*),1(3E),(3aβ,7aα)]-3,3a,5,6,7,7a-hexahydro-1-(1,5-dimethyl-5-trimethylsilyl)oxy]-3-hexenyl)-7a-methyl-4H-inden-4-one in 6 ml of dry tetrahydrofuran was added dropwise. The mixture was stirred at. −75° C. for 1 hour and quenched by addition of 1:1 mixture of 1M aqueous potassium sodium tartrate and 2M aqueous KHCO$_3$. The mixture was extracted with ethyl acetate. The organic phase was washed with saturated brine, dried (Na$_2$SO$_4$) and evaporated to dryness. The residue was chromatographed on silica gel (40–63μ) using ethyl acetate-hexane (1:15) to give 0.150 g (81%) of (3β,5Z,7E,23E)-3-[[(1,1-dimethylethyl)-dimethyl silyl]oxy]-25-[(trimethylsilyl)oxy]-9,10-secocholesta-5,7,10(19),16,23-pentane as a glass: $[α]_D^{24}+68.3°$ (c 0.18, CHCl$_3$); IR (CHCl$_3$) 1637, 838 cm$^{-1}$; $^1$H NMR (CDCl$_3$) δ0.07 (s, 6 H), 0.08 (s, 6 H), 0.10 (s, 9 H), 0.68 (s, 3 H), 0.98 (s, 9 H), 1.01 (d, J=8 Hz, 3 H), 1.28 (s, 6 H), 2.81 (m, 1 H), 3.82 (m, 1 H), 4.79 (s, 1 H), 5.02 (s, 1 H), 5.31 (s, 1 H), 5.47 (m, 1 H), 5.54 (m, 1 H), 6.09 (d, J=12 Hz, 1 H), 6.16 (d, J=12 Hz, 1 H); MS m/e 582 (M+).

EXAMPLE 21

Preparation of 25-hydroxy-16,23E-diene-cholecalciferol

To a solution of 0.144 g (0.247 mmol) of (3β,5Z,7E, 23E)-3-[[(1,1 dimethylethyl)dimethylsilyl]oxy]-25-[(trimethylsilyl)-oxy]-9,10-secocholesta-5,7,10(19),16,23-pentane in 7 ml of dry tetrahydrofuran was added 1.49 ml (1.49 mmol) of 1M tetrabutylammonium fluoride in tetrahydrofuran. The mixture was stirred at room temperature for 17 hours. After dilution with water, the mixture was extracted with ethyl acetate. The organic phase was washed with half saturated brine, saturated brine, dried (Na$_2$SO$_4$) and evaporated to dryness. The residue was purified by chromatography on silica gel. (40–63μ) using ethyl acetate-hexane (1:1.2) to afford 0.076 g (78%) of 25-hydroxy-16,23E-dienecholecalciferol as a glass: $[α]_D^{22}+62.5°$ (c 0.20. MeOH): IR (CHCl$_3$) 3605, 1637 $^1$H NMR (CDCl$_3$) δ 0.67 (s, 3 H), 1.00 (s, 3 H), 1.28 (s, 6 H), 2.56 (m, 1 H), 2.80 (m, 1 H), 3.95 (br s, 1 H), 4.82 (s, 1 H), 4.98 (s, 1 H), 5.24 (s, 1 H) 5.41–5.56 (m, 2 H), 6.04 (d, J=12 Hz, H), 6.16 (d, J=12 Hz, 1 H), MS m/e 396 (M+); UV max (EtOH) 263 nm.

EXAMPLE 22

Preparation of 4-bromo-2-methyl-2-butanol

To a solution of 6.25 g (34.5 mmol) of ethyl 3-bromopropionate in 28 ml of dry tetrahydrofuran at −20° C. was added dropwise 28.8 ml (80.6 mmol) of 2.8M methylmagnesium bromide in ether. The mixture was stirred at room temperature for 2 hours and 50 minutes then quenched by addition of 15 ml of saturated aqueous ammonium chloride. After addition of 42 ml of 1N aqueous HCl, the organic phase was separated and the aqueous phase extracted with ether. The combined organic extracts were washed with saturated brine, dried (Na$_2$SO$_4$) and evaporated to dryness. The residue was chromatographed on silica gel (40–63μ) using 30% ethyl acetate-hexane to give 2.57 g (45%) of 4-bromo-2-methyl-2-butanol as an oil: IR (CHCl$_3$) 3605 cm$^{-1}$; $^1$H NMR (CDCl$_3$) δ1.27 (s, 6 H), 1.33 (s, 1 H), 2.11 (m, 2 H), 3.51 (m, 2 H); MS m/e 151 (M$^+$—CH$_3$).

EXAMPLE 23

Preparation of 3-bromo-1,1-dimethylpropoxy)triethylsilane

To a solution of 2.56 g (15.3 mmol) of 4-bromo-2-methyl-2-butanol and 4.86 g (71.4 mmol) of imidazole in 15 ml of dry N,N-dimethylformamide at 0° C. was added dropwise 6.48 g (43.0 mmol) of chlorotriethylsilane. The mixture was stirred at room temperature for 3 hours and 20 minutes, then quenched by adding ice chips. The mixture was diluted with water and extracted with pentane. The organic phase was washed with water, saturated brine, dried (Na$_2$SO$_4$) and evaporated to dryness. The residue was chromatographed on silica gel (40–63μ) using pentane to give 4.02 g (93%) of 3-bromo-1,1-dimethylpropoxy)triethylsilane as an oil: IR (CHCl$_3$) 838 cm$^{-1}$; $^1$H NMR (CDCl$_3$) δ 0.58 (q, J=8 Hz, 6 H), 0.94 (t, J=8 Hz, 9 H), 2.03 (m, 2 H), 3.48 (m, 2 H); MS m/e 265 (M$^+$—CH$_3$).

EXAMPLE 24

Preparation of [1(R*),3aR*-(3aβ,4α,7aα)]-3a,4,5,6,7,7a-hexahydro-4-[(triethylsilyl)oxy]-β,7a-dimethyl-3H-indene-1-ethanol 4-methylbenzene sulfonate To a solution of 0.930 g (2.55 mmol) of [1(R*),3aR*-(3aβ,4α,7aα)]-3a,4,5,6,7,7a-hexahydro-4-hydroxy-β,7a-dimethyl-3H-indene-1-ethanol 4-methyl-benzenesulfonate and 1.10 g (16.2 mmol) of imidazole in 73 ml of methylene chloride at 0° C. was added dropwise 0.580 g (3.85 mmol) of chlorotriethylsilane. The mixture was stirred at room temperature for 1.5 hours then quenched by adding ice chips. The mixture was diluted with water and stirred at room temperature for 20 minutes. The organic layer was separated and the aqueous layer was extracted with methylene chloride. The combined extracts were washed with water, aqueous 1N H$_2$SO$_4$, saturated aqueous NaHCO$_3$, and saturated brine. After drying (Na$_2$SO$_4$) and evaporation, the residue was purified by chromatography on silica gel (40–63μ) using ethyl acetate-hexane (1:5) to afford 1.22 g (100%) of [1(R*),3aR*-(3aβ,4α,7aα)]-3a,4,5,6,7,7a-hexahydro-4-[(triethylsilyl)oxy]-β,7a-dimethyl-3H-indene-1-ethanol 4-methylbenzene sulfonate as an oil: [α]$_D^{20}$+46.1° (c 0.31, CHCl$_3$); IR (CHCl$_3$) 1358, 1173, 842 cm$^{-1}$; $^1$H NMR (CDCl$_3$) δ 0.55 (q, J=8 HZ, 6H), 0.84–1.02 (m, 15 H), 1.25 (m, 1 H), 1.84 (m, 2 H), 2.17 (m, 1 H), 2.38 (m, 1 H), 2.47 (s, 3 H), 3.85 (m, 1 H), 4.00 (m, 1 H), 4.09 (br s, 1 H), 5.23 (s, 1 H), 7.33 (d, J=8 Hz, 2H), 7.78 (d, J=8 Hz, 2 H); MS m/e 463 (M$^+$—CH$_3$).

EXAMPLE 25

Preparation of [1(R*),3aR*-(3aβ,4α,7aα)]-3a,4,5,6,7,7a-hexahydro-1-[1,5-dimethyl-5-[(triethylsilyl)oxy]hexyl]-4-[(triethylsilyl)oxy]-7a-methyl-3H-indene To a solution of 3.08 g (10.95 mmol) of (3-bromo-1,1-dimethylpropoxy)triethylsilane in 31 ml of tetrahydrofuran was added 0.282 g (11.6 m atom) of magnesium turnings and the mixture was heated at reflux (about 68° C.) for 3.5 hours. Then a mixture of 0.686 g (3.60 mmol) of cuprous iodide and the above mentioned Grignard solution in a separate flask was stirred at 3° C. for 30 minutes. To this was added dropwise a solution of 1.02 g (2.13 mmol) of [1(R*),(3aβ,4α,7aα)]-3a,4,5,6,7,7a-hexahydro-4-[(triethylsilyl)oxy]-β7a-dimethyl-3H-indene-1-ethanol 4-methylbenzene sulfonate and the mixture was stirred at room temperature for 40 minutes. The reaction was quenched by adding a mixture of ice chips and water. After stirring for 10 minutes, the mixture was extracted with ether. The organic phase was washed with aqueous 1N H$_2$SO$_4$, saturated aqueous NaHCO$_3$, dried (Na$_2$SO$_4$) and evaporated to dryness. The residue was chromatographed on silica gel (40–63μ) using ethyl acetate-hexane (1:15) to afford 1.80 g of [1(R*),3aR*-(3aβ,4α,7aα)]-3a,4,5,6,7, 7a-hexahydro-1-[1,5-dimethyl-5-[(triethylsilyl)oxy]hexyl]-4-[(triethylsilyl)oxy]-7a-methyl-3H-indene (contaminated with a lower alkyl side product) as an oil: IR (CHCl$_3$) 842 cm$^{-1}$; $^1$H NMR (CDCl$_3$) δ0.46–0.62 (m, 12 H), 1.16 (d, J=8Hz, 3H), 1.17 (s, 6 H), 1.86 (m, 2 H), 2.02 (m, 1 H), 2.25 (m, 1 H), 4.12 (br s, 1 H), 5.24 (br s, 1 H), MS m/e 479 (M$^+$—Et).

EXAMPLE 26

Preparation of [1(R*),3aR*-(3aβ,4aα,7aα)]-3a,4,5,6,7,7a-hexahydro-4-hydroxy-α,α,ε,7a-tetramethyl-1H-indene-1-pentanol To a solution of 1.60 g (about 1.89 mmol) of [1(R*),3aR*-(3aβ,4α,7aα)]-3a,4,5,6,7,7a-hexahydro-1-[1,5-dimethyl-5-[(triethylsilyl)oxy]hexyl]-4-[(triethylsilyl)oxy]-7a-methyl-3H-indene (contaminated with lower alkyl side product) in 5 ml of dry tetrahydrofuran was added 2.00 ml (2.00 mmol) of 1M tetrabutylammonium fluoride in tetrahydrofuran. The mixture was heated at reflux (about 8° C.) for 50 minutes. After cooling to room temperature, the mixture was diluted with water and extracted with methylene chloride. The organic phase was washed with half saturated brine, saturated brine, dried (Na$_2$SO$_4$) and evaporated to dryness. The residue was purified by a chromatography on silica gel (40–63μ) using ethyl acetate-hexane (1:1) to afford 0.420 g (79%) of [1(R*), 3aR*-(3aβ,4aα,7aα)]-3a, 4,5,6,7,7a-hexahydro-4-hydroxy-α,α,ε,7a-tetramethyl-1H-indene-1-pentanol as a glass: [α]$_D^{21}$+12.0° (c 0.25, CHCl$_3$); IR (CHCl$_3$) 3610 cm$^{-1}$; $^1$H NMR (CDCl$_3$) δ1.00 (d, J=8 Hz, 3 H), 1.06 (s, 3 H), 1.21 (s, 6 H), 2.27 (m, 1 H), 4.18 (br s, 1 H) 5.31 (s, 1 H), MS m/e 280 (M$^+$).

EXAMPLE 27

Preparation of [1(R*),3aR*-(3aβ,7aα)]-3,3a,5,6,7,7a-hexahydro-1-(5-hydroxy-1,5-dimethylhexyl)-7a-methyl-4H-inden-4-one To a solution of 0.210 g (about 0.749 mmol) of [1(R*), 3aR*-(3aβ,4α,7aα)]-3a,4,5,6,7,7a-hexahydro-4- hydroxy-α,α,ε,7a-tetramethyl-1H-indene-1-pentanol in 18 ml of dry methylene chloride was added 0.870 g (2.27 mmol) of pyridinium dichromate (98%) and 44 mg of pyridinium p-toluenesulfonate. The mixture was stirred at 25° C. for 2 hours and 15 minutes. After addition of 50 ml of ether, the mixture was stirred at 25° C. for 5 minutes and filtered. The solids were washed with saturated aqueous $CuSO_4$, water, half saturated aqueous $NaHCO_3$, and saturated brine. The organic phase was dried ($Na_2SO_4$) and evaporated to dryness. The residue was chromatographed on silica gel (40–63μ) using 35% ethyl acetate-hexane to give 0.175 g (84%) of [1(R*),3aR*-(3aβ,7aα)]-3,3a,5, 6,7,7a-hexahydro-1-(5-hydroxy-1,5-dimethylhexyl)-7a-methyl-4H-inden-4-one as a glass: $[α]_D^1 +28.2°$ (c 0.22, $CHCl_3$); IR ($CHCl_3$) 3605, 1708 $cm^{-1}$; $^1H$ NMR ($CDCl_3$) δ0.82 (s, 3 H), 1.06 (d, J=8 Hz, 3 H), 1.20 (s, 6 H), 1.76 (m, 1 H), 1.89 (m, 1 H), 2.29 (m, 2 H), 2.44 (m, 1 H), 2.84 (m, 1 H), 5.27 (m, 1 H); MS m/e 278 (M+).

EXAMPLE 28

Preparation of [1(R*),3aR*-(3aβ,7aα)]-3,3a,5,6,7,7a-hexahydro-1-(1,5-dimethyl-5-[trimethylsily)oxy]hexyl)-7a-methyl-4H-inden-4-one To a solution of 0.168 g (about 0.603 mmol) of [1(R*),3aR*-(3aβ,7aα)]-3,3a,5,6,7,7a-hexahydro-1-(5-hydroxy-1,5-dimethylhexyl)-7a-methyl-4H-inden-4-one in 24 ml of dry methylene chloride was added 0.599 g (4.27 mmol) of 1-(trimethylsilyl)-imidazole. The mixture was then stirred at 25° C. for 15 hours. The mixture was quenched by adding 6.7 ml of water and stirred at 25° C. for 20 minutes. The mixture was extracted with ethyl acetate. The organic phase was washed with saturated brine, dried ($Na_2SO_4$) and evaporated to dryness. The residue was chromatographed on silica gel (40–63μ) using ethyl acetate-hexane (1:4) to give 0.211 g (100%) of [1(R*),3aR*-(3aβ,7aα)]-3,3a,5,6, 7,7a-hexahydro-1-(1,5-dimethyl-5-[trimethylsily)oxy]hexyl)-[7a-methyl-4H-inden-4-one as a glass: $]α]_D^{20} +21.9°$ (c 0.27, $CHCl_3$): IR ($CHCl_3$) 1708, 838 $cm^{-1}$; $^1H$ NMR ($CDCl_3$) δ0.06 (s, 9 H), 0.77 (s, 3 H), 1.00 (d, J=8 Hz, 3 H), 1.13 (s, 6 H), 1.74 (m, 1 H), 1.80 (m, 1 H), 2.24 (m, 2 H), 2.40 (m, 1 H), 2.81 (m, 1 H), 5.23 (m, 1 H); MS m/e 350 (M+).

EXAMPLE 29

Preparation of (1α,3β,5Z,7E)-1,3-bis[[(1,1-dimethylethyl)dimethylsilyl]oxy]-25-[(trimethylsilyl)oxy]-9,10-secocholesta-5,7,10(19),16-tetraene To a solution of 0.581 g (about 0.930 mmol) of [3S-(1Z, 3α,5β)]-[2-[3,5-bis[[(1,1-dimethyl)dimethylsilyl]oxy]-2-methylenecyclohexylidene]ethyl]diphenyl phosphine oxide in 13 ml of dry tetrahydrofuran at −75° C. was added dropwise 0.563 ml (0.900 mmol) of 1.6M butyllithium in hexane. After stirring for 6 minutes a solution of 0.210 g (0.600 mmol) [1(R*),3aR*-(3aβ,7aα)]-3,3a,5,6,7,7a-hexahydro-1-(1,5-dimethyl-5-[(trimethylsily)oxy]hexyl)-7a-methyl-4H-inden-4-one in 8 ml of dry tetrahydrofuran was added dropwise. The mixture was stirred at −75° C. for 1 hour and 10 minutes and quenched by addition of 1:1 mixture of 1M aqueous potassium sodium tartrate and 2M aqueous $KHCO_3$. The mixture was extracted with ethyl acetate. The organic phase was washed with saturated brine, dried ($Na_2SO_4$), and evaporated to dryness. The residue was chromatographed on silica gel (40–63μ) using ethyl acetate-hexane (1:15) to give 0.358 g (83%) of (1α,3β,5Z,7E)-1,3-bis[[(1,1-dimethylethyl)dimethylsilyl]oxy]-25-[(trimethylsilyl)oxy]-9,10-secocholesta-5,7,10(19),16-tetraene as a glass: IR ($CHCl_3$) 1640, 838 $cm^{-1}$; $^1H$ NMR ($CDCl_3$) δ 0.06 (s, 12 H), 0.09 (s, 9 H), 0.68 (s, 3 H), 0.86 (s, 18 H), 1.01 (d, J=8 Hz, 3 H), 1.17 (s, 6 H), 2.03-2.28 (m, 3 H), 2.33 (m, 1 H), 2.44 (m, 1 H), 2.81 (m, 1 H), 4.19 (br s, 1 H), 4.37 (br s, 1 H), 4.88 (s, 1 H), 5.18 (s, 1 H), 5.28 (s, 1 H), 6.08 (d, J=12 Hz, 1 H), 6.24 (d, J=12 Hz, 1 H); MS m/e 714 (M+).

EXAMPLE 30

Preparation of 1,25-dihydroxy-16-ene-cholecalciferol

To a solution of 0.350 g (0.489 mmol) of (1β,3α,5Z,7E)-1,3-bis[[(1,1-dimethylethyl)dimethylsilyl]oxy]-25-[(trimethylsilyl)oxy]-9,10-secocholesta-5,7,10(19),16-tetraene in 17 ml of tetrahydrofuran was added 2.94 ml (2.94 mmol) of 1M tetrabutylammonium fluoride in tetrahydrofuran. The mixture was stirred at room temperature for 16.5 hours. After dilution with water, the mixture was extracted with ethyl acetate. The organic phase was washed with half saturated brine, saturated brine, dried ($Na_2SO_4$) and evaporated to dryness. The residue was purified by chromatography on silica gel (40–63μ) using ethyl acetate-hexane (4.5:1) to afford 0.168 g (83%) of 1,25-dihydroxy-16-ene-cholecalciferol as a glass: $[α]_D^{20} +40.0°$ (c 0.17, MeOH); IR ($CHCl_3$) 3605, 1630, 1055 $cm^{-1}$; $^1H$ NMR ($CDCl_3$) δ 0.68 (s, 3 H), 1.03 (d, J=8 Hz, 3 H), 1.20 (s, 6 H), 2.26-2.45 (m, 2 H), 2.60 (m, H), 2.83 (m, 1 H), 4.25 (br s, 1 H), 4.46 (br s, 1 H), 5.01 (s, 1 H), 5.29 (s, 1 H) 5.34 (s, 1 H), 6.11 (d, J=12 Hz, 1 H), 6.38 (s, 1 H); MS m/e 414 (M+); UV max (EtOH) 263 nm.

EXAMPLE 31

Preparation of (3β,5Z,7E)-3-[[(1,1-dimethylethyl)dimethylsilyl]oxy]-25-[(trimethylsilyl)oxy]-9,10-secocholesta-5,7,10(19),16-tetraene To a solution of 0.383 g (0.846 mmol) of [5S-(1Z)][2-[5-[[(1,1-dimethylethyl)dimethylsilyl]oxy]-2-methylenecyclohexylidene]-ethyl]diphenylphosphine oxide in 9.6 ml of dry tetrahydrofuran at −75° C. was added dropwise 0.505 ml (0.808 mmol) of 1.6M butyllithium in hexane. After 25 stirring for 6 minutes, a solution of 0.188 g (0.539 mmol) of [1(R*),3aR*-(3aβ,7aα)]-3,3a,5,6,7,7a-hexahydro-1-(1,5-dimethyl-5-[(trimethylsilyl)oxy]hexyl)-7a-methyl-4H-inden-4-one in 11 ml of dry tetrahydrofuran was added dropwise. The mixture was stirred at −75° C. for 1 hour and quenched by addition of 1:1 mixture of 1M aqueous potassium sodium tartrate and 2M aqueous $KHCO_3$. The mixture was extracted with ethyl acetate. The organic phase was washed with saturated brine, dried ($Na_2SO_4$), and evaporated to dryness. The residue was chromatographed on silica gel (40– 63μ) using ethyl acetate-hexane (1:15) to give 0.245 g (78%) of (3α,5Z,7E)-3-[[1,1-dimethylethyl)-dimethylsily]oxy]-25-[(trimethylsilyl)oxy]-9,10-secocholesta-5,7,10(19), 16-tetraene as a glass: $[α]_D^{24} +67.5°$ (c 0.20, $CHCl_3$); IR ($CHCl_3$) 1650, 1630, 841 $cm^{-1}$; $^1H$ NMR ($CDCl_3$) δ 0.04-0.16 (m, 15 H), 0.69 (s, 3 H), 0.89 (s, H), 1.02 (d, J=8 Hz, 3 H), 1.18 (s, 6 H), 2.04-2.50 (m, 7 H), 2.82 (m, 1 H), 3.84 (br s, 1 H), 4.82 (s, 1 H), 5.01 (s, 1 H), 5.28 (s, 1 H), 6.09 (d, J=12 Hz, 1 H), 6.16 (d, J=12 Hz, 1 H), MS m/e 584 (M+).

EXAMPLE 32

Preparation of 25-hydroxy-16-ene-cholecalciferol

To a solution of 0.239 g (0.408 mmol) of (3β,5Z,7E)-3-[[(1,1-dimethylethyl)-dimethylsily]oxy]-25-[(trimethylsilyl) oxy]-9,10-secocholesta-5,7,10(19),16-tetraene in 12 ml of dry tetrahydrofuran was added 2.46 ml (2.46 mmol) of 1M tetrabutylammonium fluoride in tetrahydrofuran. The mixture was stirred at room temperature for 17 hours. After dilution with water, the mixture was extracted with ethyl acetate. The organic Phase was washed with half saturated brine, saturated brine, dried (Na$_2$SO$_4$), and evaporated to dryness. The residue was purified by chromatography on silica gel (40–63μ) using ethyl acetate-hexane (1:1.2) to afford 0.135 g (83%) of 25-hydroxy-16-ene-cholecalciferol as a glass: $[\alpha]_D^{23}$ +75.4° (c 0.13, MeOH); IR (CHCl$_3$) 3605, 1650, 1625 cm$^{-1}$; $^1$H NMR (CDCl$_3$) δ 0.68 (s, 3 H), 1.02 (d, J=8 Hz, 3 H), 1.19 (s, 6 H), 2.57 (m, 1 H), 2.80 (m, 1 H), 3.96 (br s, 1 H), 4.84 (s, 1 H), 5.05 (s, 1 H), 5.29 (s, 1 H), 6.12 (d, J=12 Hz, 1 H), 6.23 (d, J=12 Hz, 1 H) MS m/e 398 (M+); UV max (EtOH) 263 nm.

EXAMPLE 33

Preparation of [1(R*),3aβ,4α,7aα]-5-[3a,4,5,6,7,7a-hexahydro-7a-methyl-4-[(trimethylsilyl)oxy]-3H-inden-1-yl]-5-methyl-2,2-dimethyl-d$_6$-2-pentyn-1-ol To a solution of 200 mg (0.688 mmol) of [1(R*), 3aR*-(3aβ,4α,7aα)]-3a,4,5,6,7,7a-hexahydro-7a-methyl-(1-methyl-3-butynyl)-4-[(trimethylsilyl)oxy]-3H-indene in 5.7 mL of dry tetrahydrofuran at −75° C. was added 0.707 mL (1.13 mmol) of 1.6M butyllithium in hexane dropwise. After stirring for 40 minutes at −75° C., 0.504 mL (6.87 mmol) of hexadeuteroacetone was added and the mixture was stirred at −75° C. for 20 minutes then at 25° C. for 1 hour and 20 minutes. The reaction was quenched at 0° C. by addition of 5 mL of a 1:1 mixture of 2M aqueous KHCO$_3$ and 1M aqueous potassium sodium tartrate. The mixture was stirred at 25° C. for 20 minutes then extracted with ethyl acetate. The organic phase was washed with saturated brine, dried (Na$_2$SO$_4$), and evaporated to dryness. The residue was chromatographed on silica gel (40–63μ) using ethyl acetate-hexane (1:5) to give 227 mg (93%) of [1(R*),3aβ,4α,7aα]-5-[3a,4,5,6,7,7a-hexahydro-7a-methyl-4-[(trimethylsilyl)oxy]-3H-inden-1-yl]-5-methyl-2,2-dimethyl-d$_6$-2-pentyn-1-ol as an oil: $[\alpha]_D^{22}$ +45.2° (c 0.25, CHCl$_3$); IR (CHCl$_3$) 3600, 2230, 840 cm$^{-1}$; MS m/e 354 (M+); $^1$H NMR (CDCl$_3$) δ 0.07 (s, 9H), 1.01 (s, 3H), 1.07 (d, J=8 Hz, 3H), 2.13–2.42 (m, 4H), 4.08 (br s, 1H) 5.34 (br s, 1H).

EXAMPLE 34

Preparation of [1(R*),3aβ,4α,7aα]-3a,4,5,6,7,7a-hexahydro-7a-methyl-1-(5-hydroxy-1-methyl-5,5-dimethyl-d$_6$-3-pentynyl)-3H-indene-4-ol To a solution of 227 mg (0.640 mmol) of [1(R*),3aβ, 4α,7aα]-5-[3a,4,5,6,7,7a-hexahydro-7a-methyl-4-[(trimethylsilyl)oxy]-3H-inden-1-yl]-5-methyl-2,2-dimethyl-d$_6$-2-pentyn-1-ol in 9 mL of dry tetrahydrofuran was added 1.92 mL (1.92 mmol) of 1M tetrabutylammonium fluoride in tetrahydrofuran. The mixture was stirred at room temperature for 50 minutes. After dilution with half saturated aqueous NaHCO$_3$, the mixture was evaporated to remove most of the solvent and extracted with ethyl acetate. The organic phase was washed with half saturated brine, dried (Na$_2$SO$_4$), and evaporated to dryness. The residue was chromatographed on silica gel (40–63 μ) using ethyl acetate-hexane (1:1) to give 163 mg (90%) of 1(R*),3aβ,4α,7aα]-3a,4,5,6,7,7a-hexahydro-7a-methyl-1-(5-hydroxy-1-methyl-5,5-dimethyl-d$_6$-3-pentynyl)-3H-indene-4-ol as a solid: m.p. 104°–106°; $[\alpha]_D^{25}$ +19.6° (c 0.49, CHCl$_3$); IR (CHCl$_3$) 3605, 2235 cm$^{-1}$; MS m/e 282 (M+); 1H NMR (CDCl$_3$) δ 1.07 (s, 3 H), 1.09 (d, J=8 Hz, 3 H), 1.78 (s, 1 H), 2.21–2.42 (m, 4H), 4.18 (br s, 1 H) 5.38 (br s, 1 H).

EXAMPLE 35

Preparation of [1(R*),3aβ,7aα]-3,3a,5,6,7,7a-hexahydro-7a-methyl-1-(5-hydroxy-1-methyl-5,5-dimethyl-d$_6$-3-pentynyl)-4H-inden-4-one To a solution of 141 mg (0.499 mmol) of [1(R*),3aβ, 4α,7aα]-3a,4,5,6,7,7a-hexahydro-7a-methyl-1-(5-hydroxy-1-methyl-5,5-dimethyl-d$_6$-3-pentynyl)-3H-indene-4-ol in 8.3 mL of dry methylene chloride was added 304 mg (3.71 mmol) of anhydrous sodium acetate and 608 mg (2.01 mmol) of 2,2'-bipyridinium chlorochromate (97%). The mixture was stirred at 25° C. for 2 hours and 30 minutes. Additional 304 mg (1.01 mmol) of 2,2'-bipyridinium chlorochromate (97%) was then added and the stirring continued for an additional 1 hour and 50 minutes. After this time, 1.1 ml of 2-propanol was introduced and 15 minutes later, the mixture was diluted with water and extracted with ether-ethyl acetate (1:1). The organic phase was washed with water, 1N H$_2$SO$_4$, half saturated aqueous NaHCO$_3$, and saturated brine. After drying (Na$_2$SO$_4$), the solution was evaporated and the residue chromatographed on silica gel (40–63μ) using ethyl acetate-hexane (1:1) to give 93 mg (67%) of [1(R*),3aβ, 7aα]-3,3a,5,6,7,7a-hexahydro-7a-methyl-1-(5-hydroxy-1-methyl-5,5-dimethyl-d$_6$-3-pentynyl)-4H-inden-4-one as a glass: $[\alpha]_D^{22}$ +35.3° (c 0.15, CHCl$_3$); IR (CHCl$_3$) 3600, 2235, 1710 cm$^{-1}$; MS m/e 280 (M+); $^1$H NMR (CDCl$_3$) δ 0.84 (s, 3 H), 1.15 (d, J=8 Hz, 3 H), 1.70–1.83 (m, 2 H, 1.85–1.95 (m, 1H), 2.45 (m, 1H), 2.85 (m, 1H), 5.37 (br s, 1 H).

EXAMPLE 36

Preparation of [1(R*), 3aβ,7aα]-3,3a,5,6,7,7a-hexahydro-7a-methyl-1-[1-methyl-5,5-dimethyl-d$_6$-5-[(trimethylsilyl)oxy]-3-pentynyl]-4H-inden-4-one To a solution of 90 mg (0.321 mmol) of [1(R*),3aβ,-7aα]-3,3a,5,6,7,7a-hexahydro-7a-methyl-1-(5-hydroxy-1-methyl-5,5-dimethyl-d$_6$-3-pentynyl)-4H-inden-4-one in 13 mL of dry methylene chloride was added 318 mg (2.27mmol) of 1-(trimethylsilyl)imidazole. The mixture was then stirred at 25° C. for 12 hours. The mixture was quenched by adding 3.5 ml of water and stirred at 25° C. for 20 minutes. The mixture was extracted with ethyl acetate. The organic phase was washed with water, saturated brine, dried (Na$_2$SO$_4$), and evaporated to dryness. The residue was chromatographed on silica gel (40–63μ) using ethyl acetate-hexane (1:4) to give 93 mg (84%) of [1(R*),3aβ, 7aα]-3,3a,5,6,7,7a-hexahydro-7a-methyl-1-[1-methyl-5,5-dimethyl-d$_6$-5-[(trimethylsilyl)oxy]-3-pentynyl]-4H-inden-4-one as a glass: MS m/e 352 (M+); $^1$H NMR (CDCl$_3$) δ 0.17 (s, 9H), 0.85 (s, 3 H), 1.15 (d, J=8 Hz, 3H), 1.73–1.84 (m, 1 H), 1.86–1.95 (m, 1 H). 2.85 (m, 1 H), 5.37 (br s, 1 H).

EXAMPLE 37

Preparation of (1α,3β,5Z,7E)-[9,10-secocholesta-5,7,10,(19),16-tetraen-23-yne-1,3,25-triyl]tris(oxy)-1,3-bis[[1,1-dimethylethyl)dimethylsilyl]oxy]-25-trimethylsilane 26,26,26, 27,27,27,$d_6$ To a solution of 136 mg (0.218 mmol) of [3S-(1Z,3α,5β)]-[2-[3,5-bis[[1,1-dimethyl)dimethylsilyl]oxy]-2-methylenecyclohexylidene]ethyl]diphenylphosphine oxide in 3 ml of dry tetrahydrofuran at −75° C. was added dropwise 0.130 ml (0.208 mmol) of 1.6M butyllithium in hexane. After stirring for 6 minutes, a solution of 48 mg (0.14 mmol) of [1(R*),3aβ,7aα]-3,3a,5,6,7,7a-hexahydro-7a-methyl-1-[1-methyl-5,5-dimethyl-$d_6$-5-[(trimethylsilyl)oxy]-3- pentynyl]-4H-indene-4-one in 1.8 ml of dry tetrahydrofuran was added dropwise. The mixture was stirred at −75° C. for 1 hour and quenched by addition of 1:1 mixture of 1M aqueous potassium sodium tartrate and 2M aqueous $KHCO_3$. The mixture was extracted with ethyl acetate. The organic phase was washed with saturated brine, dried ($Na_2SO_4$), and evaporated to dryness. The residue was chromatographed on silica gel (40–63 μ) using ethyl acetate-hexane (1:15) to give 80 mg (80%) of (1α,3β,5Z,7E)-[9,10-secocholesta-5,7,10,(19),16-tetraen-23-yne-1,3,25-triyl]tris(oxy)-1,3-bis[[1,1-dimethylethyl)dimethylsilyl]oxy]-25-trimethylsilane 26,26,26,27,27,27-$d_6$ as a glass: MS m/e 716 (M+); $^1$H NMR ($CDCl_3$) δ 0.03–0.013 (m, 6 H), 0.17 (s, 9 H), 0.70 (s, 3 H), 0.86 (s, 9 H), 0.88 (s, 9 H), 1.12 (d, J=8 Hz, 3 H), 2.46 (m, 1 H), 2.82 (m, 1 H), 4.19 (br s, 1 H), 4.37 (br s, 1 H), 4.88 (br s, 1 H), 5.17 (br s, 1 H), 5.37 (br s, 1 H), 6.10 (d, J=12 Hz, 1 H), 6.24 (d, J=12 Hz, 1 H).

EXAMPLE 38

Preparation of 26,26,26,27,27,27-hexadeutero-1α,25-dihydroxy-16-ene-23-yne-cholecalciferol To a solution of 78 mg (0.11 mmol) of (1α,3β,5Z,7E)-[9,10-secocholesta-5,7,10,(19),16-tetraen-23-yne-1,3,25-triyl]tris(oxy)-1,3-bis[[(1,1-dimethylethyl)dimethylsilyl]oxy]-25-trimethylsilane 26,26,26,27,27,27-$d_6$ in 4 ml of dry tetrahydrofuran was added 0.68 ml (0.68 mmol) of 1M tetrabutylammonium fluoride in tetrahydrofuran. The mixture was stirred at room temperature for 16 hours. After dilution with water, the mixture was extracted with ethyl acetate. The organic phase was washed with saturated brine, dried ($Na_2SO_4$), and evaporated to dryness. The residue was chromatographed on silica gel (40–63 μ) using ethyl acetate-hexane (3:1) to afford 41 mg (89%) of 26,26,26,27,27,27-hexadeutero-1α,25-dihydroxy-16-ene-23-yne-cholecalciferol as a glass: [α]$_D^{21}$+48.0° (c 0.15, MeOH); IR ($CHCl_3$) 3605, 2235 cm$^{-1}$; $UV_{max}$ (EtOH) 263 nm; MS m/e 416 (M+); $^1$H NMR ($CDCl_3$) δ 0.72 (s, 3 H), 1.12 (d, J=8 Hz, 3 H), 2.61 (m, 1 H), 2.82 (m, 1 H), 4.25 (br s, 1 H), 4.45 (br s, 1 H), 5.02 (s, 1 H), 5.34 (br s, 1 H) 5.38 (br s, 1 H) 6.10 (d, J=12 Hz, 1 H), 6.38 (d, J=12 Hz, 1 H).

EXAMPLE 39

Oral Dosage Form Soft Gelatin Capsule

| | mg/Capsule |
|---|---|
| Compound A | 0.0001–0.010 |
| Butylated Hydroxytoluene (BHT) | 0.016 |
| Butylated Hydroxyanisole (BHA) | 0.016 |
| Fractionated Coconut Oil (Neobee M-5) | 160.0 |

1. Suspend the Butylated Hydroxytoluene and Butylated Hydroxyanisole in fractionated coconut oil. Warm to about 50° C. and stir until dissolved.
2. Blanket the solution in step 1 with nitrogen and add Compound A Stir until Compound A has dissolved, maintaining the nitrogen blanket.
3. Fill in soft gelatin capsules.

Compound A is 1α,25-dihydroxy-16-ene-23-yne-cholecalciferol.

EXAMPLE 40

Topical Cream

| | mg/gm |
|---|---|
| Compound A | 0.001–1.0* |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. to 100 gm |

*Preferred range is 5–100 mg/gm.

1. Melt the Cetyl Alcohol, Stearyl Alcohol, Sorbitan Monostearate, Glyceryl Monostearate and Polyoxyethylene Stearate Blend, Polysorbate 60, Mineral Oil and a portion (60%) of Propylene Glycol together in a stainless steel container at 70° C. in a water bath.
2. Dissolve Butylated Hydroxyanisole and Propylparaben in the material from step 1 and maintain at 70°–72° C. Record the temperature of the melt.
3. Heat the Sorbitol Solution and the water in a suitable container at 70°–75° C.
4. Add the Edetate Disodium and Methylparaben to the solutions in step 3 and mix until dissolved. Record the temperature of the aqueous phase.
5. Dissolve the appropriate amount of Compound A in another portion (30%) of the Propylene Glycol in a beaker and add this to the material from step 2 while mixing. Rinse the container with the remaining (10%) of the Propylene Glycol and add this to the mixture from step 2. Maintain a nitrogen atmosphere above the product during this and subsequent steps.
NOTE: Once Compound A is added, steps 5 and 6 must be completed in rapid succession.
6. Add the oil phase from step 2 to the aqueous phase from step 5 while emulsifying with a high shear mixer. Rinse the oil phase container by withdrawing a portion of the emulsion and add this immediately to the rest of the emulsion.
7. Continue mixing and allow the product to cool to 50°–55° C. Remove an aliquot for determination of water content and droplet size. Record the result. Add additional water if necessary.

8. Continue mixing with a paddle mixer until the product cools to room temperature. Record the weight of the final product.
9. Transfer the cream to appropriate containers.

NOTE:
1. The manufacturing has to be done in amber light.
2. The final cream should be packaged within 7 days from completion of its manufacture.

It is claimed:
1. A compound of the formula

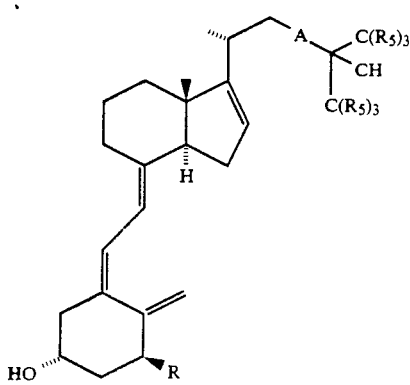

wherein R is hydrogen; R₅ is hydrogen and A is —C≡C—,

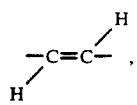

or —CH₂—CH₂—; with the proviso that when A is —C≡C—, R₅ may also be deuterium.

2. A compound in accordance with claim 1, wherein A is —C≡C—.
3. A compound in accordance with claim 2, 25-hydroxy-16-ene-23-yne-cholecalciferol
4. A compound in accordance with claim 1, wherein A is

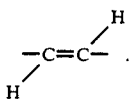

5. A compound in accordance with claim 1, wherein A is —CH₂—CH₂—.
6. A compound of the formula

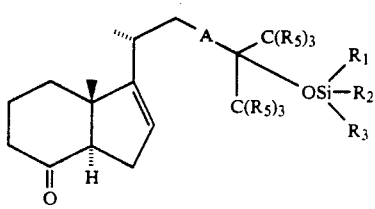

wherein A is —C≡C—,

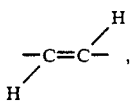

or —CH₂—CH₂—, and R₁, R₂ and R₃ are independently lower alkyl, and R₅ is hydrogen with the proviso that when A is —C≡C—, R₅ may also be deuterium.

7. A compound in accordance with claim 6 wherein A is —C≡C—.
8. The compound in accordance with claim 6, [1(R*),3aR*-3aβ,7aα)]-3,3a,5,6,7,7a-hexahydro-1-(1,5-dimethyl-5-[(trimethylsilyl)oxy]-3-hexynyl-7a-methyl-4H-inden-4-one.
9. A composition for the treatment of hyperproliferative diseases of the skin or for the treatment of neoplastic diseases comprising an effective amount of a compound of the formula

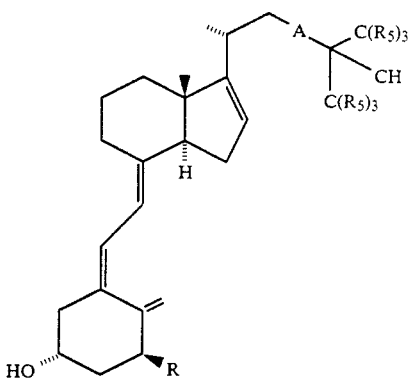

wherein R is hydrogen R₅ is hydrogen and A is —C≡C—,

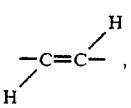

or —CH₂—CH₂—, with the proviso that when A is —C≡C—, R₅ may also be deuterium and a pharmaceutically acceptable carrier material.

10. A composition in accordance with claim 9, wherein A is —C≡C—.
11. A composition in accordance with claim 10, wherein the compound of formula I is 25-hydroxy-16-ene-23-yne-cholecalciferol.
12. A composition in accordance with claim 9 suitable for oral administration.
13. A composition in accordance with claim 9 suitable for topical administration.
14. A method for the treatment of hyperproliferative diseases of the skin which comprises administering to a warm blooded animal in need of such treatment an effective amount of a compound of the formula

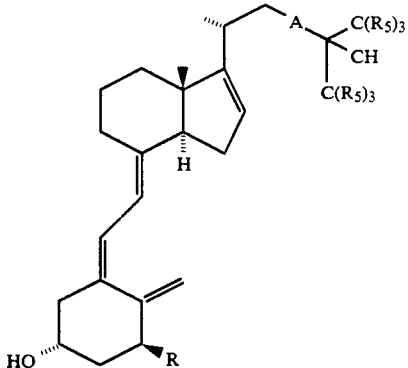

wherein R is hydrogen R₅ is hydrogen and A is —C≡C—,

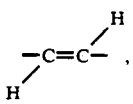

or —CH₂—CH₂, with the proviso that when A is —C≡C—, R₅ may also be deuterium.

15. A method in accordance with claim 14, wherein A is —C≡C—.

16. A method in accordance with claim 15, wherein the compound of formula I is 25-hydroxy-16-ene-23-yne-cholecalciferol.

17. A method in accordance with claim 14, wherein the hyperproliferative disorder of the skin is psoriasis.

18. A method in accordance with claim 14, wherein the compound of formula I is administered orally.

19. A method in accordance with claim 14, wherein the compound of formula I is administered topically.

20. A method for the treatment of neoplastic diseases which comprises administering to a warm blooded animal in need of such treatment an effective amount of a compound of the formula

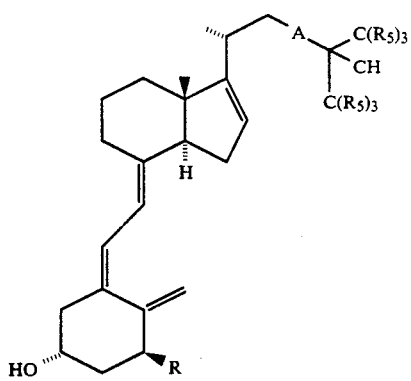

wherein R is hydrogen R₅ is hydrogen and A is —C≡C—,

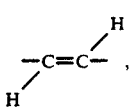

or —CH₂—CH₂—, with the proviso that when A is —C≡C—, R₅ may also be deuterium.

21. A method in accordance with claim 20, wherein A is —C≡C—.

22. A method in accordance with claim 21, wherein the compound of formula I is 25-hydroxy-16-ene-23-yne-cholecalciferol.

23. A method in accordance with claim 20, wherein the neoplastic disease is leukemia.

24. A composition for the treatment of sebaceous gland diseases comprising an effective amount of a compound of formula

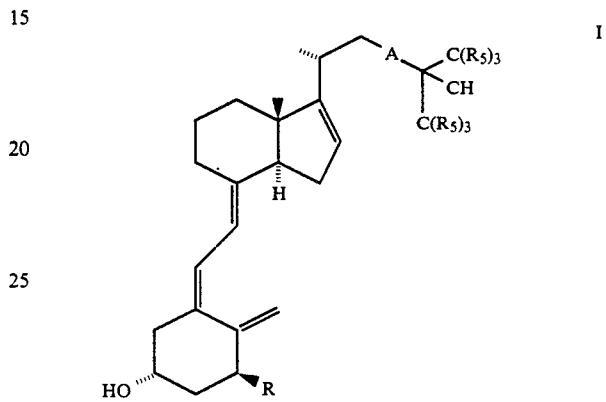

wherein R is hydrogen R₅ is hydrogen A is —C≡C—, —C=C— or —CH₂—CH₂— with the proviso that when A is —C≡C— R₅ may also be deuterium, and a pharmaceutically acceptable carrier material.

25. A compostion in accordance with claim 24, wherein A is —C≡C—.

26. A composition in accordance with claim 25, wherein the compound of formula I is 25-hydroxy-16-ene-23-yne-cholecalciferol.

27. A composition in accordance with claim 24, wherein A is —C≡C—.

28. A composition in accordance with claim 27, wherein the compound of formula I is 25-hydroxy-16,23E-diene-cholecalciferol.

29. A method for the treatment of a sebaceous gland disease of the skin which comprises administering to a warmblooded animal in need of such treatment an effective amount of a compound of the formula

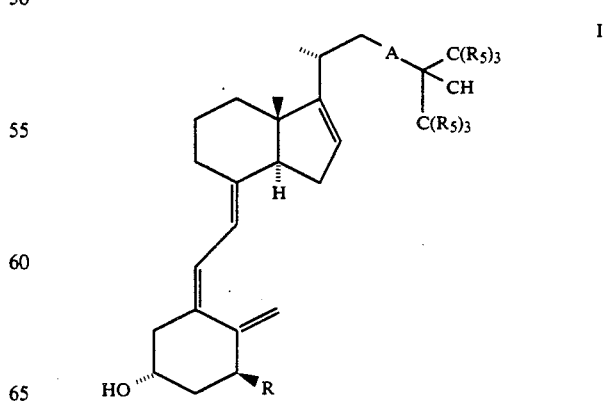

wherein R is hydrogen R₅ is hydrogen and A is —CH≡C—,

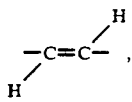

or —CH₂—CH₂— with the proviso that when A is —C≡C—, R₅ may also be deuterium.

30. A method in accordance with claim 29, wherein A is —C≡C—.

31. A method in accordance with claim 30, wherein the compound of formula I is 25-hydroxy-16-ene-23-yne-cholecalciferol.

32. A method in accordance with claim 29, wherein A is

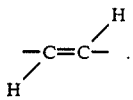

33. A method in accordance with claim 32, wherein the compound of formula I is 25-hydroxy-16,23E-diene-cholecalciferol.

34. A method in accordance with claim 29, wherein the sebaceous gland disease is acne.

35. A method in accordance with claim 29, wherein the sebaceous gland disease is seborrheic dermatitis.

36. A method in accordance with claim 29, wherein the compound of formula I is administered topically.

37. A method in accordance with claim 29 wherein the compound of formula I is administered orally.

38. A compound in accordance with claim 4, 25-hydroxy-16,23E-diene-cholecalciferol.

39. A compound in accordance with claim 5, 25-hydroxy-16-ene-cholecalciferol.

* * * * *

UNITED STATES PATENT AND TRADEMARK OFFICE
CERTIFICATE OF CORRECTION

PATENT NO. : 5,087,619

DATED : February 11, 1992

INVENTOR(S) : Enrico Giuseppe Baggiolini, Bernard Michael Hennessy, Shian-Jan Shiuey, Gary Arthur Truitt, Milan Radoje Uskokovic It is certified that error appears in the above-identified patent and that said Letters Patent is hereby corrected as shown below:

In the Abstract

In the abstract formula I should read:

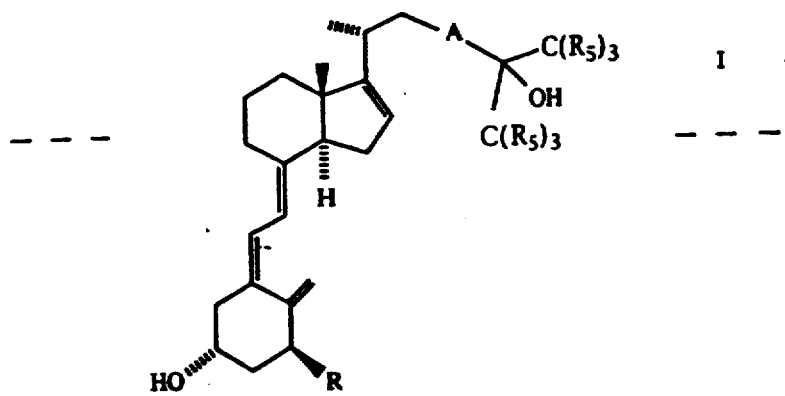

UNITED STATES PATENT AND TRADEMARK OFFICE
CERTIFICATE OF CORRECTION

PATENT NO. : 5,087,619

DATED : February 11, 1992

INVENTOR(S) : Enrico Giuseppe Baggiolini, Bernard Michael Hennessy, Shian-Jan Shiuey, Gary Arthur Truitt, Milan Radoje Uskokovic It is certified that error appears in the above-identified patent and that said Letters Patent is hereby corrected as shown below:

- Column 1, lines 16-32;
- Column 2, lines 23-38; in each occurrence formula I should read:

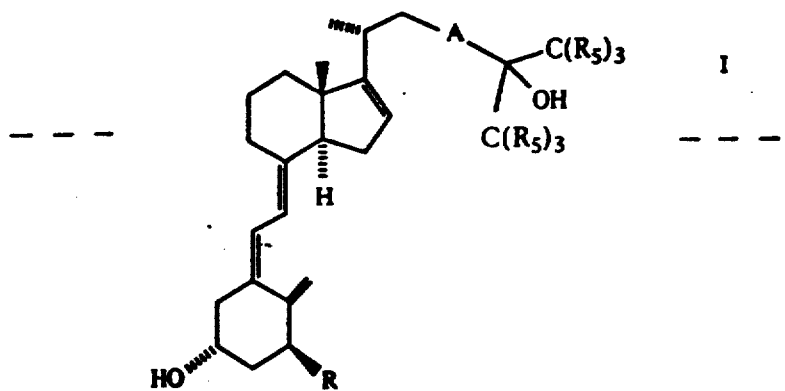

- Column 10, lines 45-55, that portion of formula XXIII reading:

UNITED STATES PATENT AND TRADEMARK OFFICE
CERTIFICATE OF CORRECTION

PATENT NO. : 5,087,619

DATED : February 11, 1992

INVENTOR(S) : Enrico Giuseppe Baggiolini, Bernard Michael Hennessy, Shian-Jan Shiuey, Gary Arthur Truitt, Milan Radoje Uskokovic It is certified that error appears in the above-identified patent and that said Letters Patent is hereby corrected as shown below:

- Column 11, lines 1-10, that portion of formula V reading:

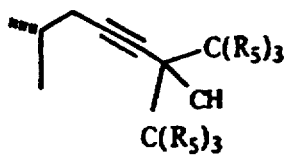   should read   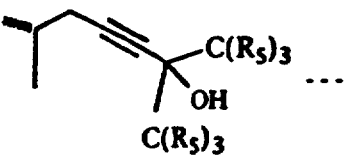

In the Claims

- Claim 1, Column 39, lines 14-29;
- Claim 9, Column 40, lines 25-40;
- Claim 14, Column 41, lines 1-16;
- Claim 20, Column 41, lines 45-60;
- Claim 24, Column 42, lines 15-29;

UNITED STATES PATENT AND TRADEMARK OFFICE
CERTIFICATE OF CORRECTION

PATENT NO. : 5,087,619

DATED : February 11, 1992

INVENTOR(S) : Enrico Giuseppe Baggiolini, et al

It is certified that error appears in the above-indentified patent and that said Letters Patent is hereby corrected as shown below:

- Claim 29, Column 42, lines 50-65; in each occurrence formula I should read:

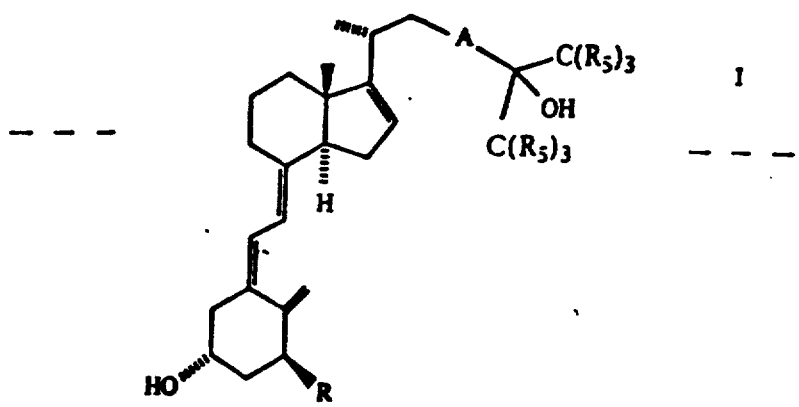

Signed and Sealed this

Sixth Day of December, 1994

Attest:

BRUCE LEHMAN

Attesting Officer

Commissioner of Patents and Trademarks